US012714076B2

(12) United States Patent
Murakami et al.

(10) Patent No.: US 12,714,076 B2
(45) Date of Patent: Aug. 25, 2026

(54) NEURODEGENERATIVE AND AMYOTROPHIC MODEL ANIMAL

(71) Applicant: TOKYO METROPOLITAN INSTITUTE OF MEDICAL SCIENCE, Tokyo (JP)

(72) Inventors: Makoto Murakami, Tokyo (JP); Tetsuya Hirabayashi, Tokyo (JP)

(73) Assignee: TOKYO METROPOLITAN INSTITUTE OF MEDICAL SCIENCE, Tokyo (JP)

( * ) Notice: Subject to any disclaimer, the term of this patent is extended or adjusted under 35 U.S.C. 154(b) by 334 days.

(21) Appl. No.: 18/702,667

(22) PCT Filed: Oct. 11, 2022

(86) PCT No.: PCT/JP2022/038495

§ 371 (c)(1),
(2) Date: Apr. 18, 2024

(87) PCT Pub. No.: WO2023/068212

PCT Pub. Date: Apr. 27, 2023

(65) Prior Publication Data

US 2024/0407344 A1 Dec. 12, 2024

(30) Foreign Application Priority Data

Oct. 22, 2021 (JP) ................................ 2021-173338

(51) Int. Cl.

*A01K 67/0276* (2024.01)
*C07K 14/47* (2006.01)
*C12N 5/10* (2006.01)
*C12N 15/85* (2006.01)
*G01N 33/50* (2006.01)

(52) U.S. Cl.

CPC .......... *A01K 67/0276* (2013.01); *C07K 14/47* (2013.01); *C12N 5/10* (2013.01); *C12N 15/8509* (2013.01); *G01N 33/502* (2013.01); *A01K 2217/075* (2013.01); *A01K 2217/15* (2013.01); *A01K 2217/206* (2013.01); *A01K 2227/105* (2013.01); *A01K 2267/0318* (2013.01); *C12N 2800/30* (2013.01)

(58) Field of Classification Search

None

See application file for complete search history.

(56) References Cited

PUBLICATIONS

Wang et al., "The Patatin-Like Phospholipase Domain Containing Protein 7 Facilitates VLDL Secretion by Modulating ApoE Stability," Hepatology 72: 1569-1585. (Year: 2020).*

Heier et al., "The phospholipase PNPLA7 functions as a lysophosphatidylcholine hydrolase and interacts with lipid droplets through its catalytic domain," Journal of Biological Chemistry 292: 19087-19098. (Year: 2017).*

Vogel et al., "Histopathology is required to identify and characterize myopathies in high-throughput phenotype screening of genetically engineered mice," Veterinary Pathology 58: 1158-1171. (Year: 2021).*

Li et al., "Disruption of the ERLIN-TM6SF2-APOB complex destabilizes APOB and contributes to non-alcoholic fatty liver disease," PLOS Genetics 16: e1008955. (Year: 2020).*

Akassoglou et al., "Brain-specific deletion of neuropathy target esterase/swisscheese results in neurodegeneration", Proc Natl Acad Sci USA, Apr. 6, 2004, vol. 101, No. 14, pp. 5075-5080.

Gregory et al., "PLA2G6-Associated Neurodegeneration", GeneReviews [Internet], 2017, pp. 1-18.

International Search Report for PCT/JP2022/038495 (PCT/ISA/210) mailed on Dec. 20, 2022.

Kienesberger et al., "Identification of an Insulin-regulated Lysophospholipase with Homology to Neuropathy Target Esterase", The Journal of Biological Chemistry, Feb. 29, 2008, vol. 283, No. 9, pp. 5908-5917.

Kienesberger et al., "Mammalian patatin domain containing proteins: a family with diverse lipolytic activities involved in multiple biological functions", Journal of Lipid Research, Apr. 2009, Supplement, pp. S63-S68.

Kmoch et al., "Mutations in PNPLA6 are linked to photoreceptor degeneration and various forms of childhood blindness", Nature Communications, 2015, vol. 6, 5614, pp. 1-10.

Melentev et al., "Human diseases associated with NTE gene", Ecological genetics, 2020, vol. 18, No. 2, pp. 229-242, https://doi.org/10.17816/ecogen16327.

Murakami et al., "Recent progress in phospholipase $A_2$ research: From cells to animals to humans", Progress in Lipid Research, 2011, vol. 50, pp. 152-192.

Read et al., "Neuropathy target esterase is required for adult vertebrate axon maintenance", The Journal of Neuroscience, Sep. 16, 2009, vol. 29, No. 37, pp. 11594-11600.

Synofzik et al., "PNPLA6 mutations cause Boucher-Neuhäuser and Gordon Holmes syndromes as part of a broad neurodegenerative spectrum", Brain, 2014, vol. 137, pp. 69-77.

Takanashi, "Pathophysiology of Glutamate Excitotoxicity Evaluated with MR Spectroscopy", FY 2017 Report on the State of Research Implementation (KAKENHI-PROJECT-16K10329), Dec. 17, 2018, pp. 1-3, total 7 pages, https://kaken.nii.ac.jp/report/KAKENHI-PROJECT-16K10329/16K103292017hokoku/.

(Continued)

*Primary Examiner* — Lora E Barnhart Driscoll

(74) *Attorney, Agent, or Firm* — Birch, Stewart, Kolasch & Birch, LLP

(57) ABSTRACT

Provided are: a neurodegenerative model animal also exhibiting amyotrophy, the neurodegenerative model animal comprising a nonhuman animal from which both the PNPLA6 and PNPLA7 genes have been deleted; and a method for screening a drug for neurodegenerative disease or a drug for a disease that causes amyotrophy, the screening method involving causing contact of a substance to be examined with said animal or with a biological sample collected from the animal, and using, as an index, an improvement effect with regards to neurodegeneration or amyotrophy of the nonhuman animal or biological sample after contact with the substance to be examined.

18 Claims, 15 Drawing Sheets

Specification includes a Sequence Listing.

(56) References Cited

PUBLICATIONS

Vrieze et al., "Genetic associations of nonsynonymous exonic variants with psychophysiological endophenotypes", Psychophysiology, Dec. 2014, vol. 51, No. 12, pp. 1300-1308.
Winrow et al., "Loss of neuropathy target esterase in mice links organophosphate exposure to hyperactivity", Nature Genetics, Apr. 2003, vol. 33, pp. 477-485.
Written Opinion of the International Searching Authority for PCT/JP2022/038495 (PCT/ISA/237) mailed on Dec. 20, 2022.
Extended European Search Report for European Application No. 22883516.1, dated Oct. 15, 2025.
Hirabayashi et al., "Hepatic phosphatidylcholine catabolism driven by PNPLA7 and PNPLA8 supplies endogenous choline to replenish the methionine cycle with methyl groups", Cell Reports, vol. 42, No. 2, Feb. 28, 2023, XP093318372, pp. 1-25 (26 pages total).
Kretzschmar et al., "The Swiss Cheese Mutant Causes Glial Hyperwrapping and Brain Degeneration in *Drosophila*," The Journal of Neuroscience, vol. 17, No. 19, Oct. 1, 1997, XP093318377, pp. 7425-7432.
McFerrin et al., "NTE/PNPLA6 is expressed in mature Schwann cells and is required for glial ensheathment of Remak fibers," Glia Wiley, vol. 65, No. 5, Feb. 16, 2017, XP071740642, pp. 804-816.
Moser et al., "Placental Failure and Impaired Vasculogenesis Result in Embryonic Lethality for Neuropathy Target Esterase-Deficient Mice", Molecular and Cellular Biology, vol. 24, No. 4, Feb. 1, 2004, XP093318363, pp. 1667-1679.
Tsap et al., "The balancing act between lipid droplets and lysosomes for membrane functionality in age-related neurodegeneration and inflammation", Progress in Lipid Research, vol. 99, Jul. 1, 2025, XP093318342, pp. 1-14.

* cited by examiner

Fig. 1

Akassoglou *et al.* Proc Natl Acad Sci U S A, 2004. 101(14): 5075-80

A
Abnormal hindlimb reflex
Control
dcKO
B
Gait abnormality
Control
dcKO
C
Grip strength (mg)
200
150
100
50
0
Control
Pnpla6 f/f; Pnpla7 f/f; Nes-Cre
5
6
7
8
9
10
weeks A
Femoral muscle
5w
8w
Control
dcKO
B
Expressions of amyotrophy markers
Control
dcKO (Pnpla6 f/f; Pnpla7 f/f; Nes-Cre)
Fbxo32 (Atrogin-1)
Trim63 (MuRF-1)
Relative mRNA expression (Fbxo32/Tbp×10³)
Relative mRNA expression (Trim63/Tbp×10³)
40000
30000
20000
10000
0
400000
300000
200000
100000
0
*
p=0.066
*p<0.05
C
Control
dKO
12w
Femoral muscle
Control
dKO
D
Control
dKO
5w
10w A
5 w
p62
DAPI
Control
dcKO
Corpus callosum
Cerebellar medulla
Medulla oblongata
B
2
3
12 w
Control
dcKO
C
DAPI
GFAP
p62
D
Control
dcKO Thin-layer chromatography (Whole brain)
Cholesterol
GalCer
Hydroxy GalCer
Decrease in sphingolipid
Sulfatide
Sphingomyelin
C: Control
K: dcKO
PE
PC
C K
2 w
C K
5 w
C K
8 w
C K
12 w

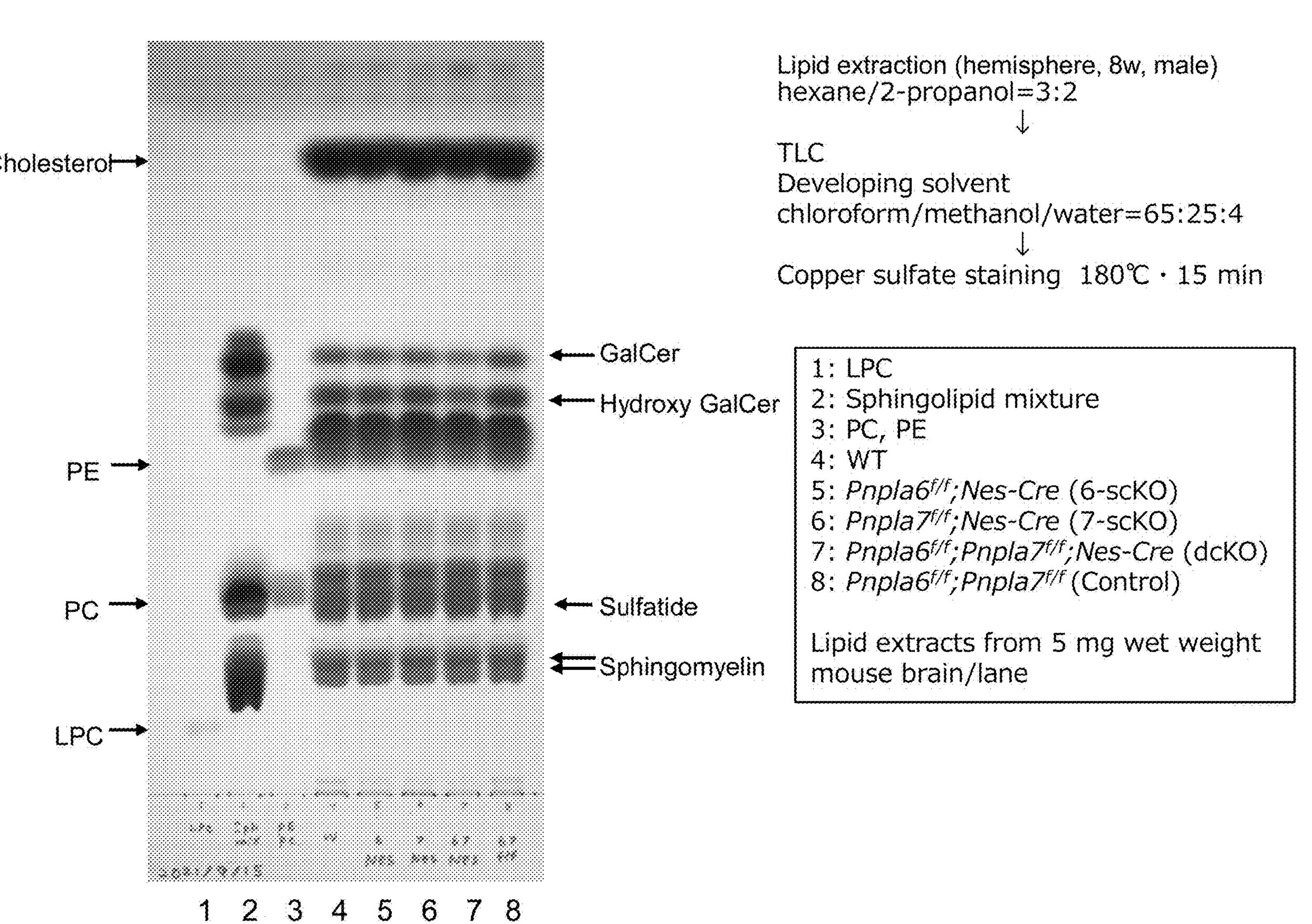
Fig. 9
Cholesterol
PE
PC
LPC
GalCer
Hydroxy GalCer
Sulfatide
Sphingomyelin
1 2 3 4 5 6 7 8
Lipid extraction (hemisphere, 8w, male)
hexane/2-propanol=3:2
↓
TLC
Developing solvent
chloroform/methanol/water=65:25:4
↓
Copper sulfate staining 180℃ · 15 min
1: LPC
2: Sphingolipid mixture
3: PC, PE
4: WT
5: *Pnpla6*$^{f/f}$;*Nes-Cre* (6-scKO)
6: *Pnpla7*$^{f/f}$;*Nes-Cre* (7-scKO)
7: *Pnpla6*$^{f/f}$;*Pnpla7*$^{f/f}$;*Nes-Cre* (dcKO)
8: *Pnpla6*$^{f/f}$;*Pnpla7*$^{f/f}$ (Control)
Lipid extracts from 5 mg wet weight mouse brain/lane Spinal cord of Pnpla6 f/f;Pnpla7 f/f;GFAP-Cre (GFAP dcKO)
KB staining
15 w
p62
15 w
Abnormally phosphorylated TDP-43-specific antibody (pS409/410)
Gray matter 8 w
50 µm Fig. 12
15 w, male
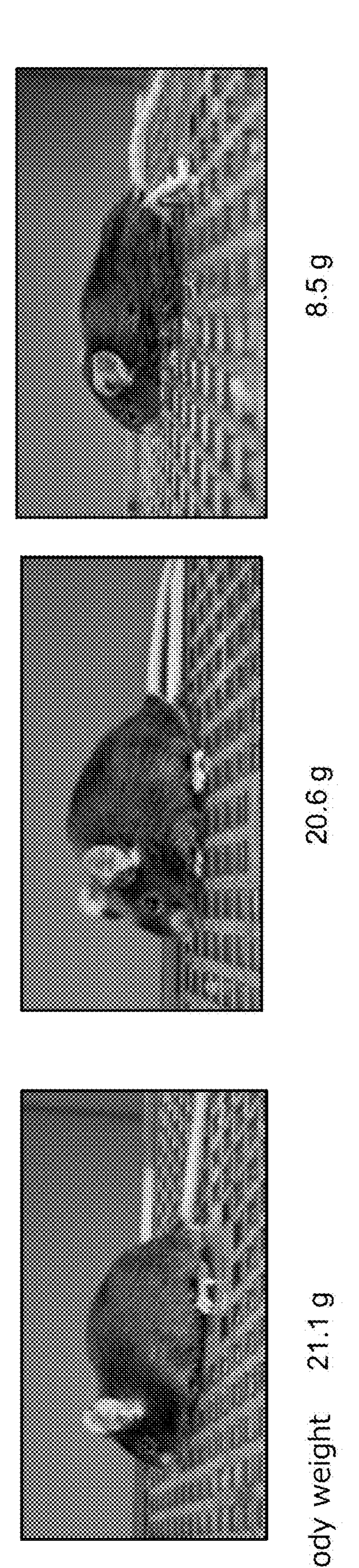
Body weight 21.1 g 20.6 g 8.5 g
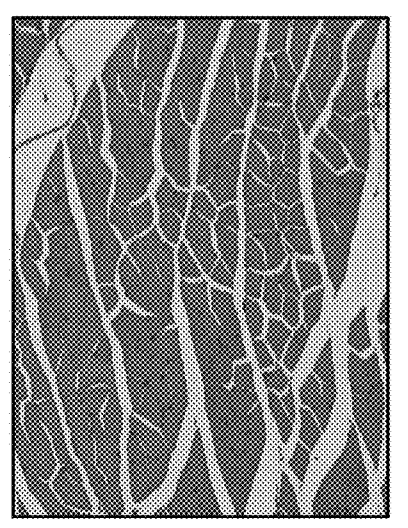
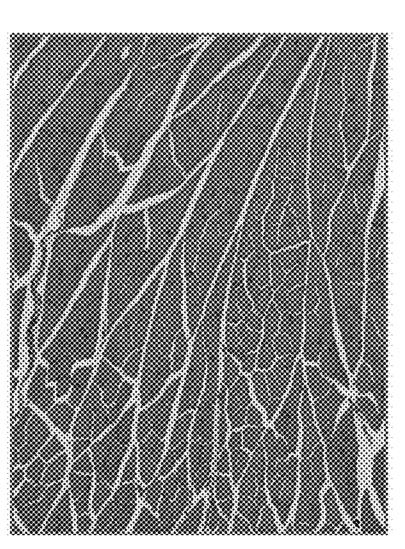
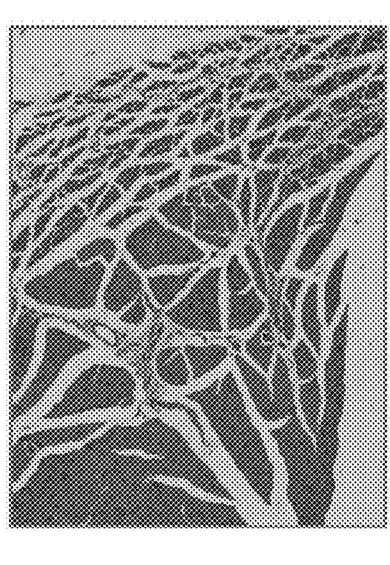
(x20) Quadriceps femoris muscle

Fig. 13

| | | *Pnpla6-Pnpla7* dcKO | *SOD1*$^{G93A}$ Tg |
|---|---|---|---|
| Whole body | Life span | 12 weeks of age or longer | Around 23 weeks of age |
| | Body weight | Max: 5 weeks of age,<br>10% decrease: 8 weeks of age | Max: 10-12 weeks of age,<br>10% decrease: 14 weeks of age |
| | Resting tremor | From around 8 weeks of age | From around 18 weeks of age |
| | Rota-rod | Abnormal from 5 weeks of age | Abnormal from 11 weeks of age |
| | Grip strength | Abnormal from 5 weeks of age | Abnormal from around 15 weeks of age |
| | Gait abnormality | From around 8 weeks of age | Abnormal from around 12 weeks of age |
| | Loss of tail suspension reflex | △ | From 8 weeks of age |
| | Curvature of the spine | From 10 weeks of age | From 20 weeks of age |
| | | | |
| Brain | GFAP staining | From 5 weeks of age | Unknown |
| | Ctip2 staining (number of layer V neurons) | Decreased at 12 weeks of age | Decreased |
| | p62-positive aggregates | From 5 weeks of age | Present |
| | Ub-positive aggregates | Not tested | Present |
| | p-TDP43-positive aggregates | Not tested | Present |
| | | | |
| Spinal cord | GFAP staining (activation of astroglia) | From 3 weeks of age | From 22 weeks of age |
| | Mac2 staining (activation of microglial) | From 3 weeks of age | From 22 weeks of age |
| | p62-positive aggregates | From 3 weeks of age | Present in motor neurons |
| | Ub-positive aggregates | Absent | Present in motor neurons |
| | ChAt staining (motor neurons) | Decreasing trend at 8 weeks of age | Decreased after 14 weeks of age |
| | p-TDP43-positive aggregates | Positive at 8 weeks of age | × at 60 days of age, positive at 90 days of age |
| | Interferon response | Significant increase at 8 weeks of age | Significant increase at 22 weeks of age |
| | | | |
| Skeletal muscle | Degeneration of the neuromuscular junction | Absent at 5 weeks of age, present at 10 weeks of age | Present from 7 weeks of age |
| | Atrophy | Present from 8 weeks of age | Present in some |

Fig. 14
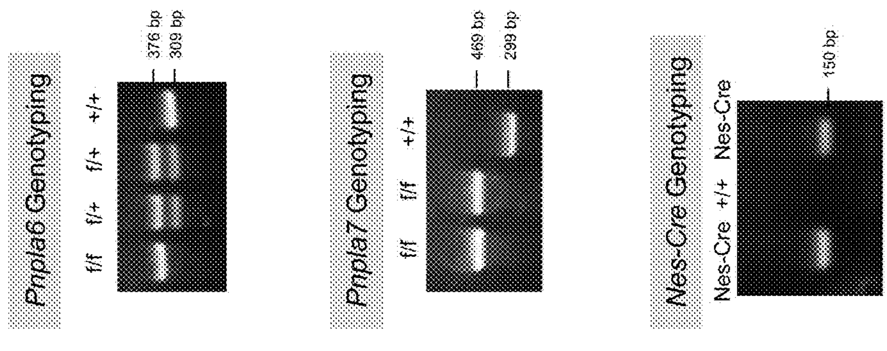
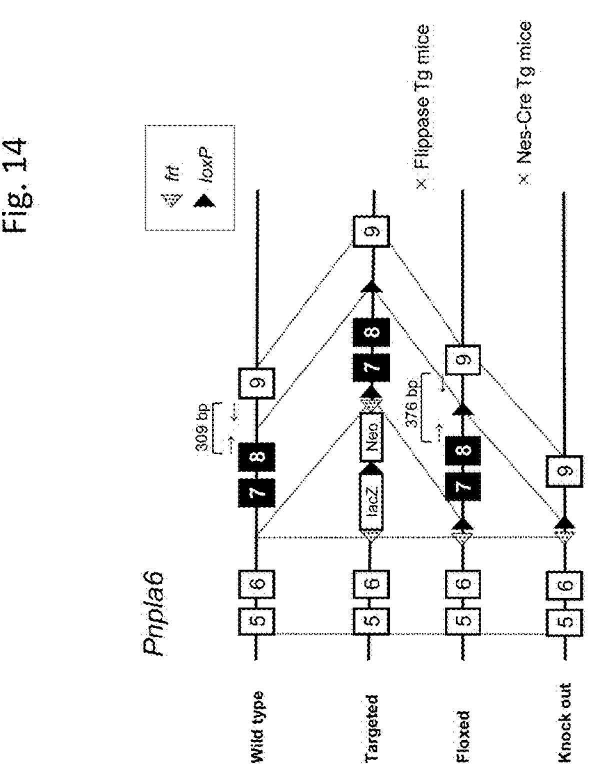
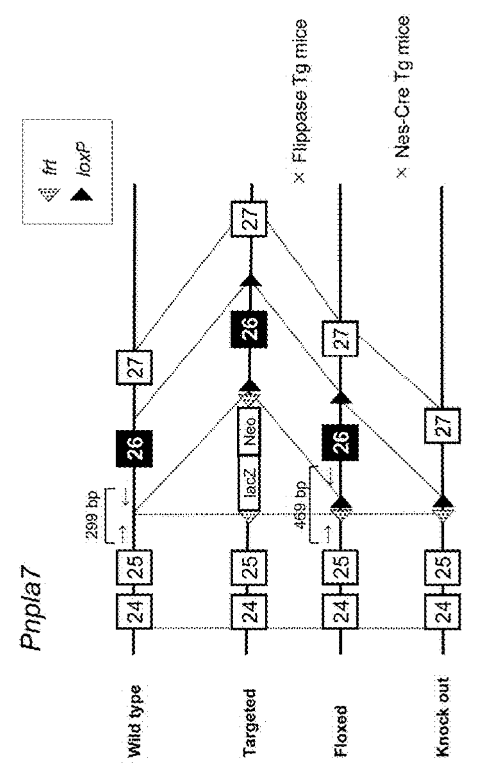

Fig. 15

| | | Deficient in PNPLA6 and PNPLA7 | | |
|---|---|---|---|---|
| | | Broad area of nervous system | Cholinergic neurons | Astrocytes |
| Whole body | Life span | From 12 weeks of age | >1 year | From 15 weeks of age |
| | Body weight | Decreased (Max : 5 weeks of age) | Decreased (Max : 20 weeks of age) | Decreased (Max : 11 weeks of age) |
| | Resting tremor | Present (8 weeks of age) | Absent | Present |
| | Rota-rod | Abnormal from 5 weeks of age | Abnormal from 30 weeks of age | Not tested |
| | Abnormal hindlimb reflex | From 8 weeks of age | From 18 weeks of age | From 8 weeks of age |
| | Curvature of the spine | From 10 weeks of age | From 10 weeks of age | Absent |
| Brain | GFAP Staining | From 5 weeks of age | To be examined | To be examined |
| | p62-positive aggregates | From 5 weeks of age | To be examined | To be examined |
| | Ub-positive aggregates | To be examined | To be examined | To be examined |
| | p-TDP-43-positive aggregates | To be examined | To be examined | To be examined |
| Spinal cord | GFAP staining (activation of astroglia) | From 3 weeks of age | From 8 weeks of age | From 8 weeks of age |
| | Mac2 staining (activation of microglial) | From 3 weeks of age | To be examined | To be examined |
| | p62-positive aggregates | From 3 weeks of age | Absent | From 8 weeks of age |
| | Ub-positive aggregates | Absent | To be examined | To be examined |
| | p-TDP-43-positive aggregates体 | From 8 weeks of age | Absent | From 8 weeks of age |
| | ChAT staining (motor neurons) | Decreased at 8 weeks of age | To be examined | To be examined |
| | Interferon response | Significant increase at 8 weeks of age | To be examined | To be examined |
| Skeletal muscle | Degeneration of the neuromuscular junction | present | To be examined | To be examined |
| | Atrophy | From 8 weeks of age | From 36 weeks of age | From 8 weeks of age |

NEURODEGENERATIVE AND AMYOTROPHIC MODEL ANIMAL

REFERENCE TO ELECTRONIC SEQUENCE LISTING

The application contains a Sequence Listing which has been submitted electronically in .XML format and is hereby incorporated by reference in its entirety. Said .XML copy, created on Oct. 7, 2022, is named "G3000WO_Sequence Listing.xml" and is 23,491 bytes in size. The sequence listing contained in this.XML file is part of the specification and is hereby incorporated by reference herein in its entirety.

TECHNICAL FIELD

The present invention relates to a neurodegenerative model animal with amyotrophy, deficient in both the PNPLA6 gene and the PNPLA7 gene, and to a method for screening a drug for a neurodegenerative disease, etc. using the animal.

BACKGROUND ART

The PNPLA (patatin-like phospholipase domain-containing) family is a series of lipid-metabolizing enzymes that share the patatin domain as the catalytic domain (FIG. 1), and there are 9 molecular species in humans. These enzymes use neutral lipids and phospholipids as substrates, and many congenital metabolic disorders caused by mutations or single nucleotide polymorphisms in the genes encoding these enzymes are known. For example, PNPLA1 causes congenital ichthyosis due to abnormal acylceramide synthesis, PNPLA2/ATGL (adipose triglyceride lipase) causes neutral lipid storage disease, and PNPLA3 causes fatty liver (Non-patent literature 1).

PNPLA6-9 are a group of enzymes with phospholipase $A_2$ activity and lysophospholipase activity, all of which use phospholipids as substrates (FIG. 1). PNPLA6 is expressed in many tissues, including the nervous system and kidney, and localizes to the endoplasmic reticulum membrane via the N-terminal transmembrane domain. It is also often referred to as neuropathy target esterase (NTE) because it was identified as a target gene for the induced delayed neuropathy caused by organophosphorus insecticides. Mutations in the human PNPLA6 gene cause a broad clinical spectrum of inherited diseases including cerebellar ataxia, spasticity, neuropathy, hypogonadism, retinitis pigmentosa, and atrophy of the choroid and retina, and they have been found to be associated with Boucher-Neuhauser syndrome, Laurence-Moon syndrome, Oliver-McFarlane syndrome, SPG39, a hereditary spastic paraplegia, and else (Non-patent literature 2, 3). Mitochondrial myopathy with lactic acidosis (MMLA) is a known human disease involving PNPLA8/iPLA2γ mutations. Neurodegenerative diseases caused by mutations in PNPLA9/PLA2G6/iPLA2β are also called PLA2G6-associated neurodegeneration (PLAN), including infantile neuroaxonal dystrophy (INAD), neurodegeneration with brain iron accumulation (NBIA) type 2, and dystonia-parkinsonism syndrome PARK14 (Non-patent literature 4).

Since the PNPLA family is also widely found in plants and yeast, it is assumed to be a group of enzymes involved in lipid metabolism essential for life activities. Among these molecular species, PNPLA6 and PNPLA7 have primary structures with high amino acid sequence homology to each other (FIG. 1) and exhibit lysophospholipase activity in vitro (Non-patent literature 5). In studies using gene-deficient mice, systemic deficiency of the PNPLA6 gene results in embryonic lethality due to placental abnormality, whereas heterozygous deficient mice are considered a model of hyperactivity disorder with increased spontaneous locomotor activity (Non-patent literature 6). On the other hand, when the PNPLA6 gene is deleted in a central nervous system-specific manner, neurodegeneration of the hippocampus, thalamus, cerebellar Purkinje cells, and the like begins to occur by around 6 weeks of age, and abnormal hindlimb reflexes and decreased motor coordination and motor learning are observed at 5 months of age (Non-patent literature 7, 8). However, the molecular mechanisms leading to such neurodegeneration have not yet been fully elucidated.

Meanwhile, with regard to PNPLA7, although there is a report that a single nucleotide polymorphism correlates with one of the endophenotypes of psychiatric disorders (Non-patent literature 9), the association of mutations in the PNPLA7 gene with human congenital metabolic disorders and neurodegeneration is not well understood.

CITATION LIST

Non-Patent Literature

Non-patent literature 1] Murakami M, Taketomi Y, Miki Y, Sato H, Hirabayashi T, Yamamoto K. Recent progress in phospholipase $A_2$ research: from cells to animals to humans. *Prog Lipid Res* 50: 152-192, 2011

[Non-patent literature 2] Synofzik M, et al. PNPLA6 mutations cause Boucher-Neuhauser and Gordon Holmes syndromes as part of a broad neurodegenerative spectrum. *Brain* 137: 69-77, 2014

[Non-patent literature 3] Kmoch S, Majewski J, et al. Mutations in PNPLA6 are linked to photoreceptor degeneration and various forms of childhood blindness. *Nat Commun* 6, 5614, 2015

[Non-patent literature 4] Gregory A, Kurian M A, Maher E R, Hogarth P, Hayflick S J. PLA2G6-associated neurodegeneration. *Gene Reviews* (registered trademark) [Internet], 2017

[Non-patent literature 5] Kienesberger P C, Lass A, Preiss-Landl K, Wolinski H, Kohlwein S D, Zimmermann R, Zechner R. Identification of an insulin-regulated lysophospholipase with homology to neuropathy target esterase. *J. Biol. Chem.* 283: 5908-5917, 2008

[Non-patent literature 6] Winrow C J et al. Loss of neuropathy target esterase in mice links organophosphate exposure to hyperactivity. *Nat Genet* 33: 477-85, 2003

[Non-patent literature 7] Akassoglou K, Malester B, Xu J, Tessarollo L, Rosenbluth J, Chao M V. Brain-specific deletion of neuropathy target esterase/swisscheese results in neurodegeneration. *Proc Natl Acad Sci USA* 101: 5075-5080, 2004

[Non-patent literature 8] Read D J, Li Y, Chao M V, Cavanagh J B, Glynn P. Neuropathy target esterase is required for adult vertebrate axon maintenance. *J Neurosci* 29: 11594-11600, 2009

[Non-patent literature 9] Vrieze S I, Malone S M, Pankratz N, et al. Genetic associations of nonsynonymous exonic variants with psychophysiological endophenotypes. *Psychophysiology* 51: 1300-1308, 2014

SUMMARY OF INVENTION

Technical Problem

The above background has prompted the development of a tool useful for elucidating the pathogenesis of neurodegeneration and neurogenic amyotrophy and for evaluating the efficacy of a therapeutic drug.

Solution to Problem

The present inventors have made a thorough study to solve the above problem, and in order to analyze the function of a lysophospholipase which is structurally similar to PNPLA6 and PNPLA7 in the central nervous system, mice that simultaneously lack the PNPLA6 gene and the PNPLA7 gene in a nervous system-specific manner were created and their phenotypes were analyzed, and found that neurodegeneration accompanied by severe amyotrophy was caused and the mice had short lifespans.

The present invention is based on the above findings.

Thus, the present invention is as follows.

[1] A neurodegenerative disease model animal with amyotrophy, comprising a nonhuman animal deficient in both PNPLA6 gene and PNPLA7 gene.

[2] The animal according to [1], in which PNPLA6 gene and PNPLA7 gene are deleted in a neuron- and/or glial cell-specific manner.

[3] The animal according to [1], wherein amyotrophy is neurogenic amyotrophy.

[4] The animal according to [3], wherein a symptom of the neurodegenerative disease is accompanied by at least one selected from the group consisting of a shortened lifespan, weight loss, impaired motor skill, gait abnormality, resting tremor, spasticity, abnormal hindlimb reflex, amyotrophy, curvature of the spine, loss of motor neurons, degeneration of neuromuscular junction, activation of astrocytes, activation of microglia, accumulation of p62-positive aggregates, accumulation of phosphorylated TDP-43 aggregates, and a decrease in a group of sphingolipids in the myelin sheath.

[5] The animal according to [2], wherein the neuron is a cholinergic neuron.

[6] The animal according to [5], wherein a symptom of the neurodegenerative disease is accompanied by at least one selected from the group consisting of a shortened lifespan, weight loss, impaired motor skill, gait abnormality, abnormal hindlimb reflex, amyotrophy, curvature of the spine, activation of astrocytes, and activation of microglia

[7] The animal according to [2], wherein the glial cell is in the astroglial lineage.

[8] The animal according to [7], wherein a symptom of the neurodegenerative disease is accompanied by at least one selected from the group consisting of a shortened life span, weight loss, impaired motor skill, gait abnormality, resting tremor, spasticity, abnormal hindlimb reflex, amyotrophy, curvature of the spine, loss of motor neurons, degeneration of neuromuscular junction, activation of astrocytes, activation of microglia, accumulation of p62-positive aggregates, and accumulation of phosphorylated TDP-43 aggregates.

[9] The animal according to [1], wherein the nonhuman animal is a mouse, rat, rabbit, dog, cat, pig, marmoset, or monkey.

[10] A model cell or organoid for a neurodegenerative disease with amyotrophy, comprising an animal cell deficient in both the PNPLA6 gene and the PNPLA7 gene.

[11] The model cell or organoid according to [10], in which the PNPLA6 gene and the PNPLA7 gene are deleted in a neuron- and/or glial cell-specific manner.

[12] The model cell or organoid according to [11], wherein the neuron is a cholinergic neuron.

[13] The model cell or organoid according to [11], wherein the glial cell is in the astroglial lineage.

[14] A method for screening a drug for a neurodegenerative disease, the method comprising the steps of: contacting a test substance with the animal according to any one of [1]-[9], a biological sample collected from said animal, or the model cell or organoid according to any one of [10]-[13]; and if an effect of amelioration of neurodegeneration is obtained in said nonhuman animal, biological sample or model cell after its contact with the test substance, then selecting the test substance as a drug for a neurodegeneration disease.

[15] A method for screening a drug for a disease with amyotrophy, the method comprising the steps of: contacting a test substance with the animal according to any one of [1]-[9], a biological sample collected from said animal, or the model cell or organoid according to any one of [10]-[13]; and if an effect of amelioration of amyotrophy is obtained in said nonhuman animal, biological sample, or model cell or organoid after its contact with the test substance, then selecting the test substance as a drug for a disease with amyotrophy.

[16] The method according to [15], wherein amyotrophy is neurogenic amyotrophy.

[17] The method according to [16], wherein the disease with neurogenic amyotrophy is at least one selected from the group consisting of amyotrophic lateral sclerosis, primary lateral sclerosis, frontotemporal lobar degeneration, spinal muscular atrophy, spinal progressive muscular atrophy, spinobulbar muscular atrophy, spastic paraplegia, and multifocal motor neuropathy.

Advantageous Effects of Invention

The present invention provides a model animal that produces neurodegeneration with severe amyotrophy. This model animal is expected to be a novel and useful tool of a non-conventional type for elucidating the pathogenesis of neurodegeneration and neurogenic amyotrophy and for evaluating the efficacy of a therapeutic drug.

BRIEF DESCRIPTION OF DRAWINGS

Figure 1:
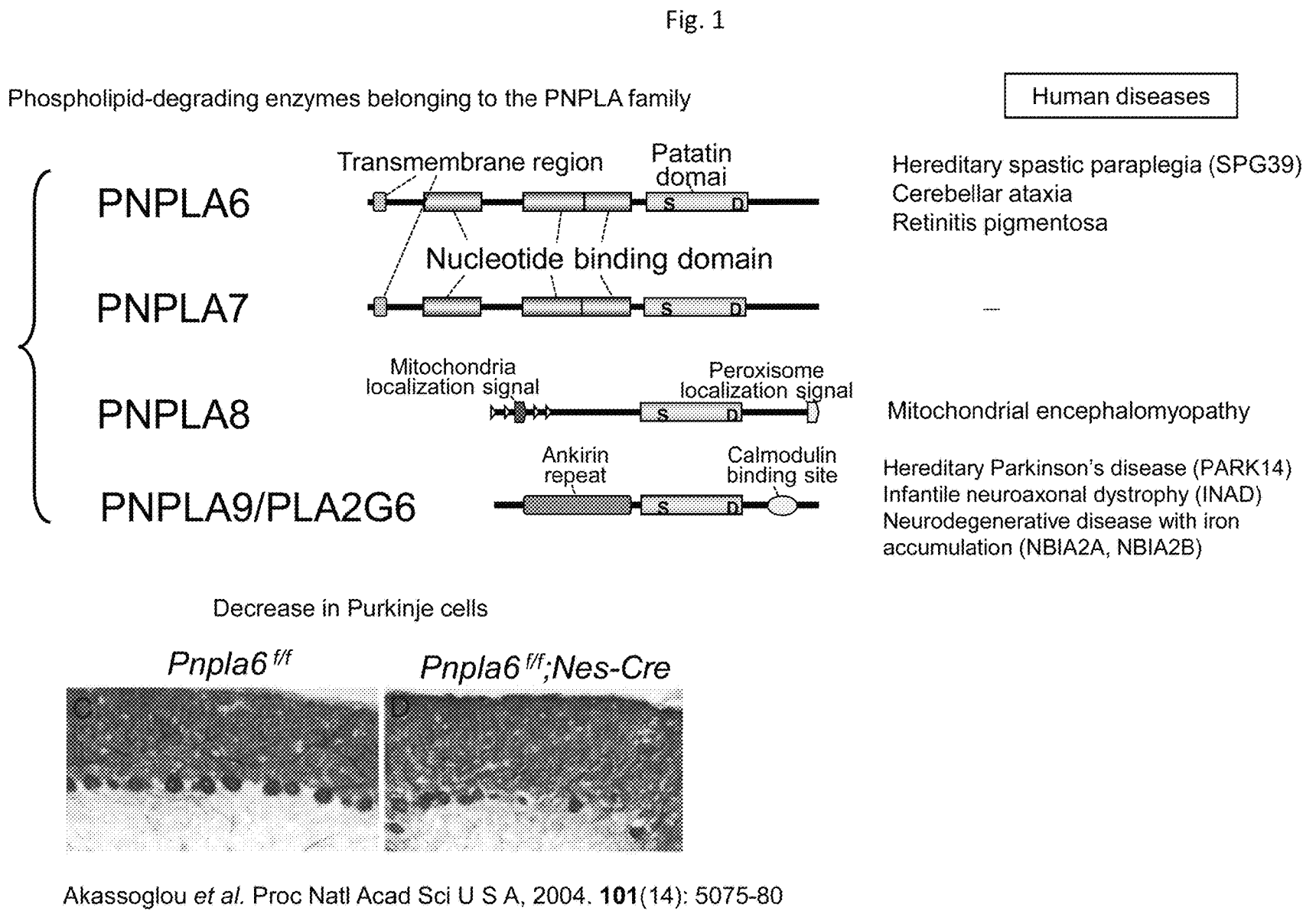

FIG. 1 A figure showing the relationship between the PNPLA family and human neurodegenerative diseases.

Paraffin section, 5 μm, KB staining, 12 weeks old female, lumbar spinal cord

Figure 8:
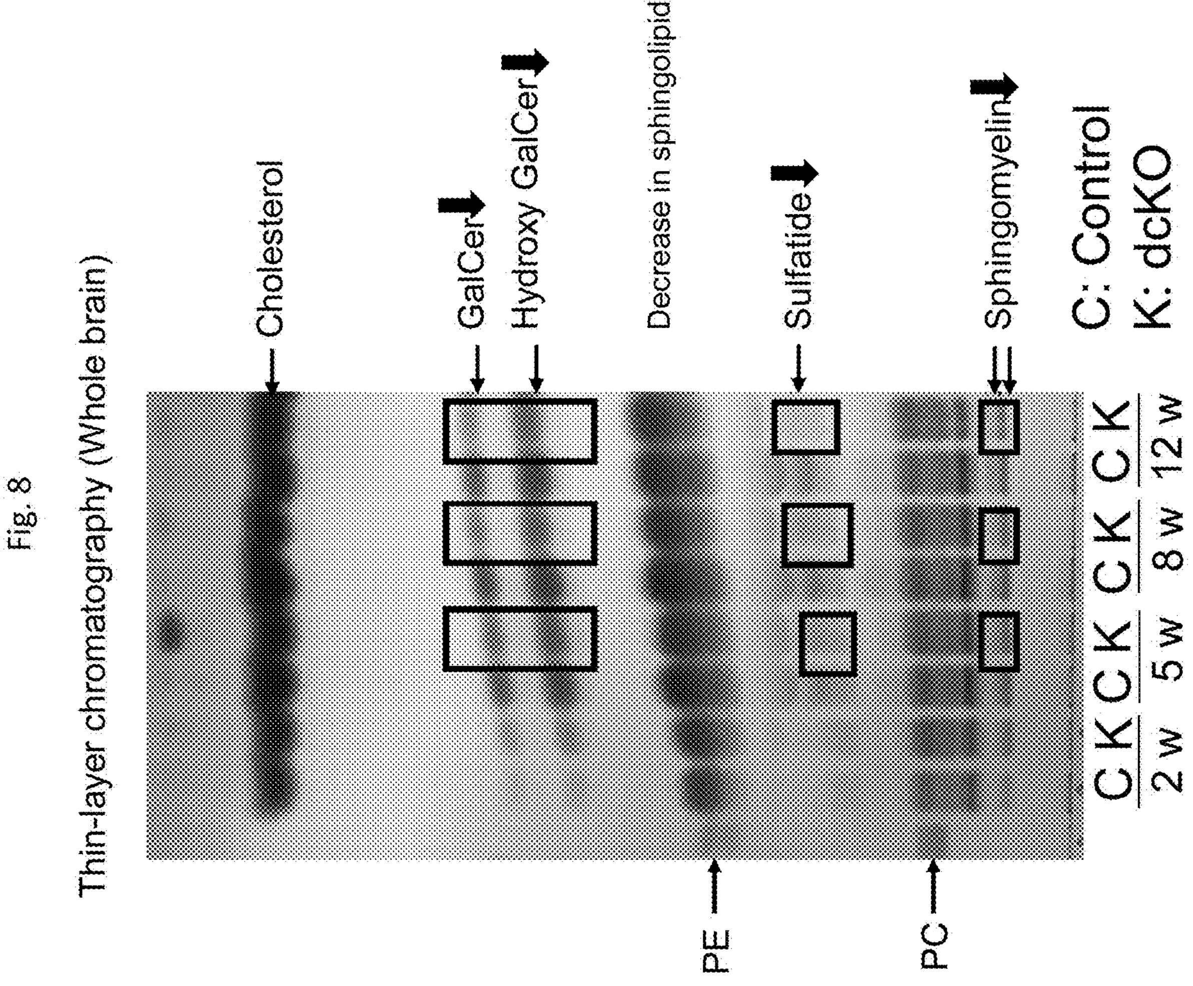

FIG. 8 A figure showing decreases (changes over time) in major lipids in myelin sheath of brain of a PNPLA6- and PNPLA7-deficient mouse.

In dcKO, decreases in GalCer (galactosylceramide), Hydroxy GalCer (hydroxy galactosylceramide), and Sulfatide were observed. This result suggests that the myelin sheath may also be abnormal in dcKO.

FIG. 9 Figures showing that decreases in the major lipids in myelin sheath do not occur in the brains of mice lacking PNPLA6 or PNPLA7 alone. The decreases in the major sphingolipids that occur in the myelin sheath of dcKO mouse are absent in mice lacking PNPLA6 alone (6-scKO) or PNPLA7 alone (7-scKO).

Figure 10:
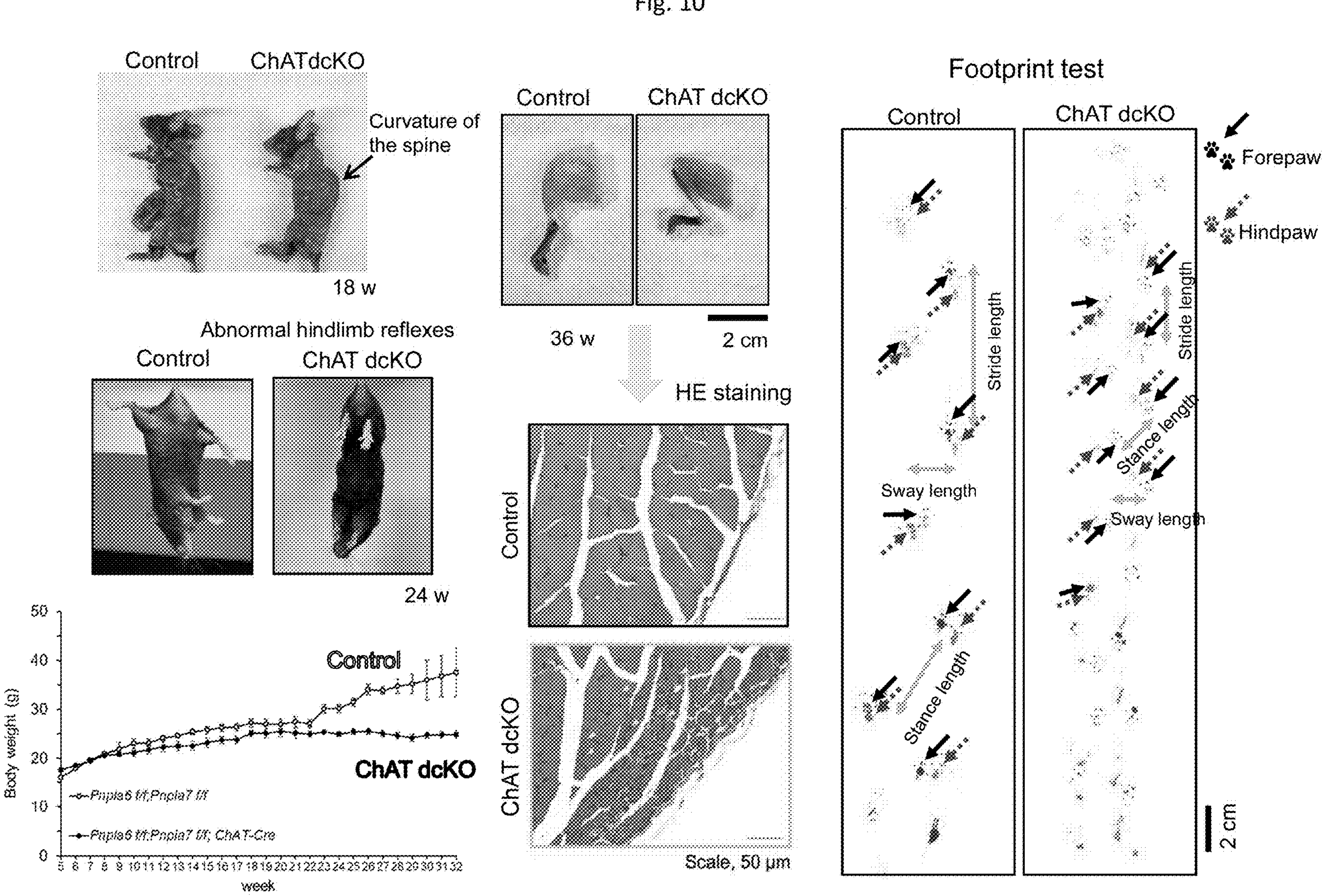

FIG. 10 A figure showing phenotypes of ChAT dcKO mice.

Figure 11:
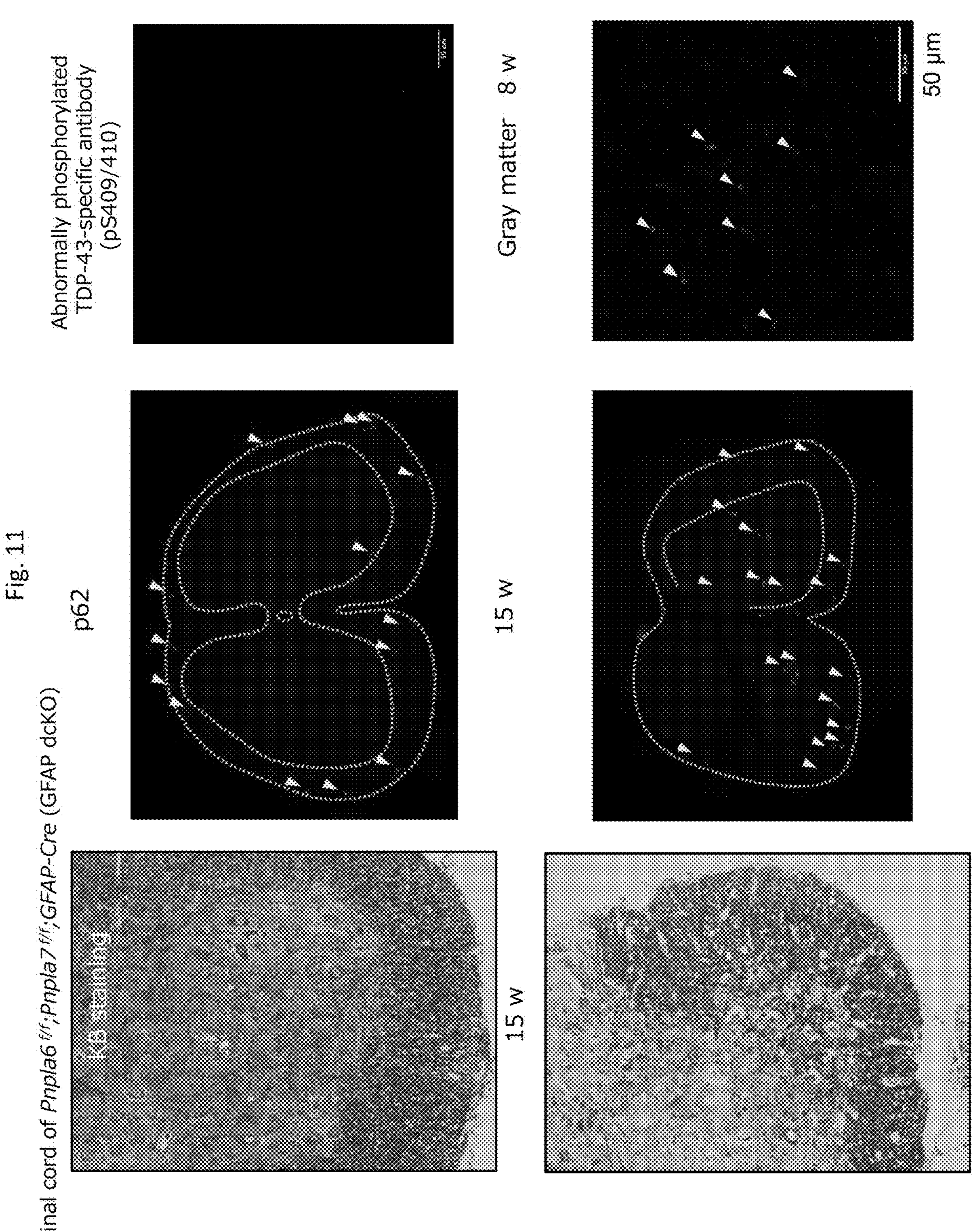

FIG. 11 Figures showing phenotypes of GFAP dcKO mice. In the KB stained images, the upper left panel shows an individual with a normal appearance, while the lower left panel shows an individual with a markedly abnormal appearance, weight loss, and degeneration of motor neurons in the spinal cord.

FIG. 12 Figures showing phenotypes of GFAP dcKO mice.

FIG. 13 A table showing phenotypic comparison between a PNPLA6- and PNPLA7-deficient mouse and a typical conventional ALS model mouse (SOD$^{G93A}$ Tg mouse).

FIG. 14 Figures showing targeting vectors for generating PNPLA6 and PNPLA7-deficient mice, as well as the results of genotyping PCRs.

FIG. 15 A table showing phenotypic comparison among dcKO, ChAT dcKO, and GFAP dcKO mouse strains.

DESCRIPTION OF EMBODIMENTS

The present invention relates to a neurodegenerative disease model animal with amyotrophy, comprising a non-human animal deficient in both the PNPLA6 gene and the PNPLA7 gene.

In another aspect, the present invention relates to a model cell for a neurodegenerative disease with amyotrophy, comprising an animal cell deficient in both the PNPLA6 gene and the PNPLA7 gene.

Genetically engineered mice simultaneously lacking two types of lysophospholipases (PNPLA6 and PNPLA7) that degrade lysophospholipids in the central nervous system developed neurodegeneration accompanied by p62-positive aggregates in broad areas of the brain and spinal cord, and died prematurely following denervation at the neuromuscular junction, severe amyotrophy, and a decline in muscle strength and motor function. When both enzymes were deleted in a cholinergic neuron-specific or astroglia-specific manner, neurodegeneration and amyotrophy similarly progressed, albeit at different onset times. These model animals are expected to be novel and useful tools of a non-conventional type for elucidating the pathogenesis of neurodegeneration and neurogenic amyotrophy and for evaluating the efficacy of a therapeutic drug.

Herein, "PNPLA6" is used to refer to a protein (enzyme) and "Pnpla6" is used to refer to a gene, but a gene encoding PNPLA6 is sometimes referred to as "the PNPLA6 gene" for the sake of explanation. "Pnpla6" and "the PNPLA6 gene" are synonymous.

The same also applies to "PNPLA7" and "Pnpla7".

1. Generation of Double-Knockout Animal or Model Cell for the PNPLA6 and PNPLA7 Genes For the purpose of analyzing the function of a specific gene in individual animals such as mice, gene knockout animals that lack this gene are used.

However, in the present invention, if the targeted PNPLA6 and PNPLA7 genes are systemically deleted, it will result in embryonic lethality, which will make it impossible to perform the desired analysis. Therefore, in the present invention, this problem is circumvented by deleting the genes only in a specific tissue or cell type. In the present invention, it is possible to cause the defect in, for example, the central nervous system, the peripheral nervous system, a specific neuronal population, or glial cells.

For example, a genetically engineered animal is generated by inserting loxP sequences by gene targeting method or genome editing method at both ends of specific regions of the PNPLA6 and the PNPLA7 genes to be deleted, and then the animal is crossed with a transgenic animal expressing the Cre recombinase under the control of a tissue-specific promoter or a cell type-specific promoter.

In the resulting individual animals, genes are deleted only at a site where the tissue-specific or cell type-specific promoter acts.

In one aspect of the present invention, for example, as illustrated in the examples, a targeting vector (FIG. 14A), which consists of a FRT-LacZ-loxP-Neo-FRT-loxP sequence inserted upstream of exon 7 of the PNPLA6 gene and a loxP sequence inserted downstream of exon 8, is introduced into ES cells to select homologous recombinant ES cells. Chimeric mice and F1 mice are generated, and crossed with Flippase-overexpressing mice to generate Pnpla6 flox/+ mice (Pnpla6 f/+ mice). Pnpla6 f/+ mice are further crossed with each other to obtain Pnpla6 f/f mice.

For PNPLA7 gene-deficient mice, for example, a targeting vector (FIG. 14B) for the deletion of exon 26 using the Cre-loxP system is generated, introduced into ES cells to generate chimeric mice, and F1 mice with confirmed germ line transmission are crossed with Flippase-overexpressing mice to establish Pnpla7 flox/+ mice (Pnpla7 f/+ mice). Pnpla7 f/+ mice are crossed with each other to obtain Pnpla7 f/f mice. Pnpla6 f/f and Pnpla7 f/f can also be produced by genome editing technique using a complex containing CRISPR/Cas9, Cas9 Nikase, ZFN (zinc finger nuclease), TALEN, or other nuclease.

Furthermore, double conditional knockout mice are established by crossing with transgenic mice that specifically express the Cre recombinase in nervous system cells under the control of a predetermined promoter.

In one aspect, the present invention relates to a model cell for a neurodegenerative disease with amyotrophy (hereinafter, simply referred to as a "model cell"), including an animal cell in which both the PNPLA6 and PNPLA7 genes have been knocked out.

In the present invention, a phenotype of the animal that lacks the PNPLA6 and PNPLA7 genes in a neuron- and/or glial cell-specific manner is amyotrophy, mainly neurogenic amyotrophy.

In the above neurodegenerative disease model, phenotypes related to symptoms of the neurodegenerative disease include a shortened lifespan, weight loss, impaired motor skill, gait abnormality, resting tremor, spasticity, abnormal hindlimb reflex, amyotrophy, curvature of the spine, loss of motor neurons, degeneration of neuromuscular junction, abnormal activation of astrocytes, activation of microglia, accumulation of p62-positive aggregates, accumulation of phosphorylated TDP-43 aggregates, a decrease in a group of sphingolipids in the myelin sheath, and a combination thereof.

Also in another aspect of the present invention, the PNPLA6 and PNPLA7 genes can be deleted in a cholinergic neuron-specific manner, i.e., a neuron-specific manner. Phenotypes associated with the neurodegenerative disease in this case include a shortened lifespan, weight loss, impaired motor skill, gait abnormality, resting tremor, spasticity, abnormal hindlimb reflex, amyotrophy, curvature of the spine, loss of motor neurons, degeneration of neuromuscular junction, abnormal activation of astrocytes, activation of microglia, and a combination thereof.

Yet in another aspect of the present invention, the PNPLA6 and PNPLA7 genes can be deleted in an astroglial cell-specific manner, i.e., a glial cell-specific manner. Phenotypes associated with the neurodegenerative disease in this case include a shortened lifespan, weight loss, impaired motor skill, gait abnormality, resting tremor, spasticity, abnormal hindlimb reflex, amyotrophy, curvature of the spine, loss of motor neurons, degeneration of neuromuscular junction, abnormal activation of astrocytes, activation of microglia, accumulation of p62-positive aggregates, accumulation of phosphorylated TDP-43 aggregates, and a combination thereof.

The animal cells in which both the PNPLA6 and PNPLA7 genes are knocked out can be collected from the aforementioned PNPLA6 and PNPLA7 gene double knockout animals, or genome editing to knock out the PNPLA6 and PNPLA7 genes or knock down their gene expressions by RNA interference can be also used in a target cell.

Both genome editing and RNA interference are well-known techniques in the art, and those skilled in the art can select and implement them as appropriate. These techniques can be performed using the following kit, or in accordance with known literature.

Genome Editing: Jinek M, Chylinski K, Fonfara I, Hauer M, Doudna J A, Charpentier E: A programmable dual-RNA-guided DNA endonuclease in adaptive bacterial immunity. Science 337: 816-821, 2012.

Patent on use of CRISPR/Cas9 technique (JP6692856): Methods and compositions for RNA-dependent target DNA modification and RNA-dependent transcriptional regulation RNA interference: Dharmacon RNAi research reagents (Horizon Discovery), Silencer Select siRNA (Thermo Fisher Scientific), etc.

Examples of the target animal cells include neurons, glial cells, and iPS cells and stem cells that can differentiate into various types of cells.

Here, when iPS cells are used as the target animal cells, their source is not particularly limited and may be purchased. Alternatively, four genes (Oct3/4, Sox2, Klf4, and c-Myc), the so-called Yamanaka factors, can be introduced, for example, into fibroblasts using an appropriate vector (e.g., retrovirus vector) and cultured for several weeks to obtain reprogrammed cells (pluripotent stem cells).

After deleting the PNPLA6 and PNPLA7 genes in iPS cells, the cells are cultured in the presence of a proliferative factor and various differentiation factors to obtain predetermined cells. For example, when the cells are differentiated into motor neurons, serum-free floating culture of embryoid body-like aggregates with quick reaggregation (Egawa N, Kitaoka S, Tsukita K, et al., Drug screening for ALS using patient-specific induced pluripotent stem cells. Sci Transl Med 4: 145ra104, 2012) or the like can be used. They may also be differentiated into bundle-like nerve fibers by culturing them in a culture chamber of a microdevice and coupled to cultured myocytes to give a neuromuscular tissue model.

The thus-obtained cells can be used as model cells for a neurodegenerative disease with amyotrophy.

The cells include both cells derived from the aforementioned biological sample, and cells obtained by double knockout of the PNPLA6 and PNPLA7 genes from the target animal cells. According to the present invention, a cell derived from a biological sample collected from the aforementioned nonhuman animal can also be understood as a "model cell" in a broad sense.

Furthermore, the present invention also allows a cell assembly and an organoid derived from the aforementioned cell to be used as a neurodegenerative disease model organoid. An "organoid" is an organ (cell assembly) created in three dimensions in vitro, for example, in a test tube, etc. An organoid can be formed by self-assembly of tissue cells, ES cells, or iPS cells cultured in three dimensions, utilizing the self-renewal and differentiation abilities of these cells.

The model cell or organoid of the present invention is a cell or an organoid, which is deficient in the PNPLA6 and PNPLA7 genes in a neuron- and/or glial cell-specific manner. The model cell or a neuron constituting the model organoid is, for example, a cell lacking the PNPLA6 and PNPLA7 genes in a cholinergic neuron-specific manner, a cell lacking the PNPLA6 and PNPLA7 genes in an astroglial cell-specific manner, i.e., a glial cell-specific manner, or the like.

2. Screening Method

A screening method of the present invention comprises the steps of: contacting a test substance with a nonhuman animal deficient in the PNPLA6 and PNPLA7 genes; and if an effect of amelioration of neurodegeneration, an effect of amelioration of amyotrophy, an effect of amelioration of motor function, or more than one of these effects is obtained in said nonhuman animal after its contact with the test substance, then selecting the test substance as a drug for a neurodegenerative disease or a drug for a disease with amyotrophy.

In another aspect, a screening method of the present invention comprises the steps of: contacting a test substance with a biological material collected from the nonhuman animal deficient in the PNPLA6 and PNPLA7 genes or the aforementioned model cell; detecting an effect of amelioration of neurodegeneration, an effect of amelioration of amyotrophy, or both effects; and using the obtained result as an indicator to select a drug for a neurodegenerative disease or a drug for a disease with amyotrophy.

In the present invention, the test substances as candidates for a drug (candidate substances) are not limited to any particular substances, and examples thereof include peptides, proteins, nucleic acids, lipids, sugars, non-peptide compounds, synthetic compounds, fermentation products, cell extracts, and plant extracts. These compounds may be novel compounds or known compounds. These test substances may form salts. Salts of the test substances are salts formed with physiologically acceptable acids (e.g. inorganic acids) or bases (e.g. organic acids), preferably physiologically acceptable acid addition salts.

As such a salt, for example, a salt formed with an inorganic acid (e.g., hydrochloric acid, phosphoric acid, hydrobromic acid, sulfuric acid, etc.) or a salt formed with an organic acid (e.g., acetic acid, formic acid, propionic acid, fumaric acid, maleic acid, succinic acid, tartaric acid, citric acid, malic acid, oxalic acid, benzoic acid, methanesulfonic acid, benzene sulfonic acid, etc.) is used.

As the test substance, a single substance may be tested independently or a mixture (including a library, etc.) may be tested. Examples of a library including multiple test substances include a synthetic compound library (e.g. a combinatorial library) and a peptide library (e.g. a combinatorial library).

"Contacting" means a state in which the test substance is administered to the nonhuman animal, a state in which the test substance is added to the biological material or the aforementioned model cell, a state in which culture is performed in the presence of the test substance, or the like.

A method for contacting the test substance with the nonhuman animal may be, for example, administration. The method of administration is not particularly limited and may be, for example, oral or parenteral administration (injection, application, etc.), and may be selected as appropriate to the species of animal, the properties of the test substance, etc. The dosage of the test substance can be selected as appropriate to the method of administration, the properties of the test substance, etc. When the test substance is brought into contact with the nonhuman animal itself, it may be performed, for example, in a state where the test substance is inoculated into the animal by injection, etc., or applied to the skin, etc.

Examples of the state where the test substance is added to a biological material, a model cell, or an organoid include addition of the test substance to a culture product of the cell, and addition of the test substance to a body fluid, blood or a lymph fluid, etc. The term "culture product" refers to either cells, a culture solution, or a cell extract. The phrase "culturing in the presence of the test substance" means that culture is performed under the conditions of bringing the cells and the test substance into contact with each other. Contact between the test substance and the aforementioned cells can be performed, for example, by adding the test substance to a cell culture medium and any buffer (e.g., HEPES buffer, phosphate buffer, phosphate-buffered saline, etc.) and incubating the cells for a certain period of time.

The concentration of the test substance added to the culture product depends on its characteristics (type of compound, solubility, toxicity, etc.) but can be selected appropriately, for example, in the range of 1 nM-1,000 μM. The incubation time is, for example, 24 hours to 1 week.

The nonhuman animal (test animal) and the control animal to which the test substance is administered are usually, but not limited to, nonhuman animals of the same species. It is preferable that the test animal and the control animal be from the same litter, and more preferable that they be of the same sex and the same age. Examples of the nonhuman animal include a rodent such as a mouse, a rat, and a guinea pig, as well as a rabbit, a chicken, a goat, a cow, a horse, a dog, a cat, a pig, a marmoset, and a monkey.

In the present invention, a test substance is brought into contact with the nonhuman animal to examine regeneration, re-growth, repair, augmentation, recovery, etc. of a degenerated nerve or an atrophied muscle, or prevention of nerve degeneration or amyotrophy (these are collectively referred to as "amelioration").

"Regeneration" means to regenerate lost nerve function, "repair" means to correct and restore partially lost nerve or muscle function, "augmentation" means to further enhance a nerve or muscle function already possessed, and "prevention" means to prevent a decline in survival or function of nerves, or a decline in function of muscles, already possessed.

Examples of items to evaluate whether the test substance has shown an effect of amelioration such as regeneration or repair of degenerated nerves, recovery from amyotrophy, augmentation of muscle strength, or the like, include a change in PNPLA6 and/or PNPLA7 expression level or activity, a decrease in degenerated neurons in the cranial nervous system, suppression of a decrease in motor neurons existing in the anterior hom of the spinal cord, a decrease in activation of astrocytes and microglia, a decrease in the expression level of an amyotrophy marker gene, an increase in muscle mass (re-growth of atrophied skeletal muscle), proliferation of muscle satellite cells and their differentiation into myoblasts, and prolonged lifetime.

These evaluations can be performed using techniques such as observation of appearance of the animal, pathohistological analysis, genetic engineering analysis, biochemical analysis, and motor coordination analysis. As to the effect of promoting a function in a neurodegenerative disease or the effect of promoting a function in a disease with amyotrophy, if at least one of the effects including increased PNPLA6 and/or PNPLA7 expression level or activity, increased muscle strength, increased muscle mass, reduced motor impairment, improved electrophysiological findings in electromyography, reconstruction of neuromuscular junction, amelioration of paralysis of the hindlimbs or limbs or amelioration of respiratory muscle paralysis, etc. is observed, the test substance is considered to be effective in regenerating, repairing, augmenting, or preventing deterioration of nerve function and thus selected as a drug for a neurodegenerative disease (agent for promoting neurological function). When at least one of the above effects is observed, the drug is selected as a drug for a disease with amyotrophy (agent for ameliorating amyotrophy).

Herein, "with amyotrophy" includes both "caused by amyotrophy" and "accompanied by amyotrophy".

The nonhuman animal or model cell deficient in the PNPLA6 and PNPLA7 genes used in the present invention can be an animal or model cell in which the PNPLA6 and PNPLA7 genes are homozygously knocked out or an animal or model cell in which the PNPLA6 and PNPLA7 genes are heterozygously knocked out, but since systemic homozygous knockout animals die early after birth as described above, it is preferable to use a nerve-specific homozygous knockout animal or heterozygous knockout animal.

According to the present invention, in addition to the nonhuman animal or model cell lacking the PNPLA6 and PNPLA7 genes, a nonhuman animal or model cell having the PNPLA6 and PNPLA7 genes but with mutations that render these genes nonfunctional or hypofunctional can also be used. Mutation means a change (deletion, substitution, or insertion, etc.) of a part of the full-length sequence of the PNPLA6 or PNPLA7 genes, generating the gene that contains a sequence that does not correctly encode a protein with PNPLA6 activity or a protein with PNPLA7 activity i.e., the gene that does not have the original function of the PNPLA6 or PNPLA7 gene.

Furthermore, according to the present invention, when a nonhuman animal having the PNPLA6 and PNPLA7 genes deleted or mutated, or a biological material or a model cell obtained from a nonhuman animal having the PNPLA6 and PNPLA7 genes deleted or mutated is used, a wild-type nonhuman animal in which the PNPLA6 and PNPLA7 genes are not knocked out or mutated, or a cell in which the PNPLA6 and PNPLA7 genes are not knocked out or mutated can be used as a comparison control.

Examples of the biological material collected from the nonhuman animal include a nonhuman animal-derived cell (neuron, glial cell, skeletal muscle cell, etc.), a body fluid, blood, a lymph fluid, and a cerebrospinal fluid.

Examples of the neurodegenerative disease include, but are not particularly limited to, hereditary spastic paraplegia, spinocerebellar degeneration, Parkinson's disease, Parkinson's syndrome (including multiple system atrophy and progressive supranuclear palsy), Alzheimer's disease, dementia with Lewy bodies, and corticobasal degeneration.

Examples of the disease with amyotrophy (including diseases caused by amyotrophy and diseases accompanied by amyotrophy) include, but are not particularly limited to, amyotrophic sclerosis (ALS), frontotemporal lobar degeneration (FTLD), spinal muscular atrophy (SMA), spinal progressive muscular atrophy (SPMA), spinal and bulbar muscular atrophy (SBMA), and multifocal motor neuropathy.

EXAMPLES

Hereinafter, the present invention will be described further in detail by way of examples. The scope of the present invention, however, should not be limited to these examples.

Example 1

1. Method

Generation of Neuron-Specific Pnpla6- and Pnpla7-Deficient Mice

For Pnpla6-deficient mice, a targeting vector (PG00244_Z_7_C03), which consisted of a FRT-LacZ-loxP-Neo-FRT-loxP sequence inserted upstream of exon 7 of PNPLA6 gene and a loxP sequence inserted downstream of exon 8, was purchased from the European Conditional Mouse Mutagenesis Program (EUCOMM) and introduced into RENKA strain of C57BL/6N-derived ES cells to select homologous recombinant ES cells (FIG. 14A). Chimeric mice and F1 mice were generated, and crossed with Flippase-overexpressing mice to generate Pnpla6 flox/+ (hereafter Pnpla6 f/+) mice. These mice were further crossed with each other to obtain Pnpla6 f/f mice.

For PNPLA7 gene-deficient mice, a targeting vector (FIG. 14B) for the deletion of exon 26 that contains an amino acid sequence predicted to be the active site of the enzyme by use of the Cre-loxP system was created, and then introduced into ES cells TT2 to generate chimeric mice. F1 mice with confirmed germ line transmission were crossed with Flippase-overexpressing mice to establish Pnpla7 flox/+ (hereafter Pnpla7 f/+) mice and backcrossed for 10 or more generations to C57BL/6N genetic background. Pnpla7 f/+ mice were crossed with each other to obtain Pnpla7 f/f mice.

These were further crossed with transgenic mice that expressed the Cre recombinase specifically in nervous system cells downstream of the Nestin promoter to establish (i) $Pnpla6^{f/f}$; Nes-Cre, (ii) $Pnpla7^{f/f}$; Nes-Cre, and (iii) $Pnpla6^{f/f}$; $Pnpla7^{f/f}$; Nes-Cre (hereinafter, double conditional KO=dcKO) and use them for analysis.

Nucleotide sequences of the primers used for PCR to genotype the genetically engineered mice are shown in Table 1.

TABLE 1

| | | |
|---|---|---|
| Pnpla6-F | ACTTGCCTGTTATGTGTAGG (SEQ ID NO: 1) | WT allele: 309 bp |
| Pnpla6-R | TGATGACATCAAGGATGCTC (SEQ ID NO: 2) | flox allele: 376 bp |
| Pnpla7-F | CCCTGGTTCAATTCCCAGTA (SEQ ID NO: 3) | WT allele: 299 bp |
| Pnpla7-R | GGAGTTTGCATGACCACAGA (SEQ ID NO: 4) | flox allele: 469 bp |
| NesCre-F | CCTTCCTGAAGCAGTAGAGCA (SEQ ID NO: 5) | 150 bp |
| NesCre-R | GCCTTATTGTGGAAGGACTG (SEQ ID NO: 6) | |

Gene Expression Analysis mRNA expression levels were analyzed by real-time PCR using TaqMan probe method. Primers and Universal Probe Library (UPL) were designed by ProbeFinder (gene names, forward primers, reverse primers, and UPL numbers are listed in this order).

For the gene expression levels, Hprt1 was used as the endogenous control gene, and Tbp was used as the endogenous control gene only for the detection of the amyotrophy marker.

```
Hprt1:
                                    (SEQ ID NO: 7)
tgatagatccattcctatgactgtaga,
                                    (SEQ ID NO: 8)
aagacattctttccagttaaagttgag, #22

Pnpla6:
                                    (SEQ ID NO: 9)
tgccagcatctatgtggttc,
                                   (SEQ ID NO: 10)
cacacactccttcccatcag, #66

Pnpla7:
                                   (SEQ ID NO: 11)
ggagggggtggagctaga,
                                   (SEQ ID NO: 12)
cgcccacactctgctagtgc, #105

Tbp:
                                   (SEQ ID NO: 13)
ggggagctgtgatgtgaagt,
                                   (SEQ ID NO: 14)
ccaggaaataattctggctcat, #97

Fbxo32:
                                   (SEQ ID NO: 15)
agtgaggaccggctactgtg,
                                   (SEQ ID NO: 16)
gatcaaacgcttgcgaatct, #53

Trim63:
                                   (SEQ ID NO: 17)
tgacatctacaagcaggagtgc,
                                   (SEQ ID NO: 18)
tcgtcttcgtgttccttgc, #83
```

Immunohistochemistry

Mouse tissues were fixed overnight in 4% paraformaldehyde, embedded in paraffin, and thinly sliced to a thickness of 5-10 μm for histochemical staining and immuno-antibody staining. For immunostaining of the paraffin section, antigen retrieval treatment was performed with 10 mM citrate buffer (pH 6.0) at 105° C. for 20 minutes in an autoclave apparatus. Only the staining of the neuromuscular junction was performed on a 40-μm thick frozen section. For histochemical staining, Kluver-Barrera staining was performed.

The antibodies and their dilution conditions used for the immunostaining were as follows.

Figure 5:
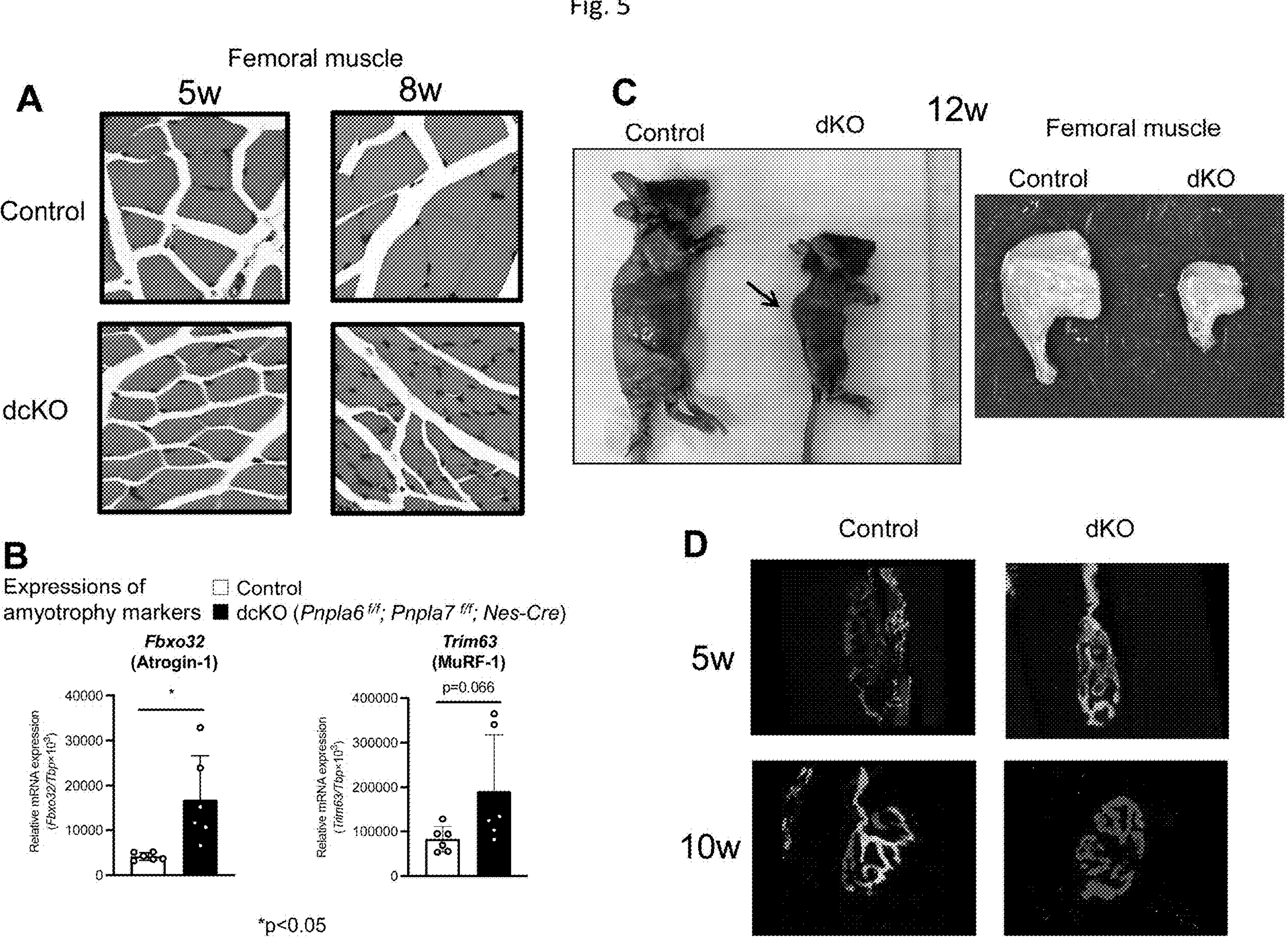
FIG. 5 Figures showing amyotrophy and denervation at the neuromuscular junction in PNPLA6- and PNPLA7-deficient mice.
Figure 6:
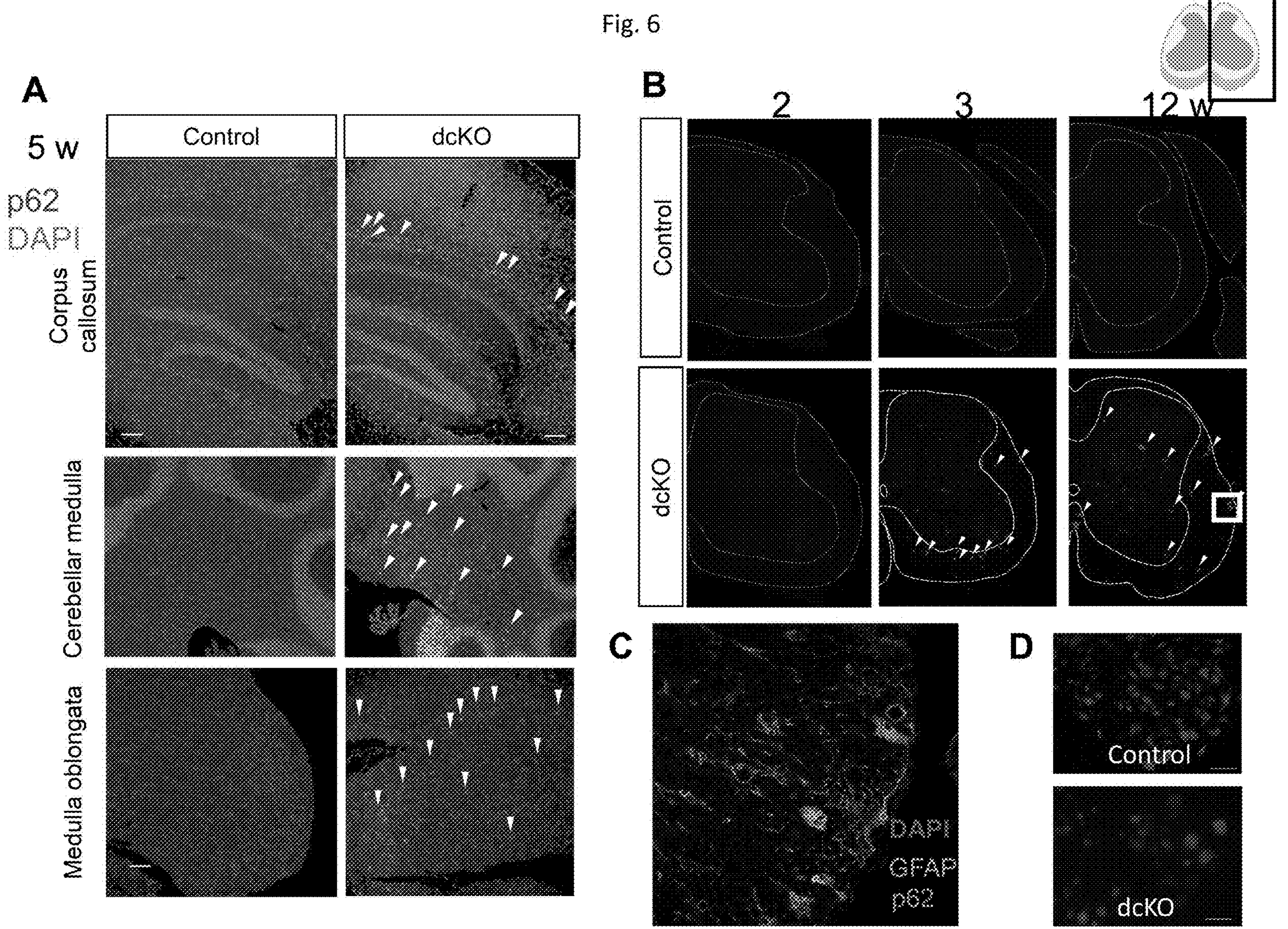
FIG. 6 Figures showing neurodegeneration accompanied by p62-positive aggregates in the brain white matter and spinal cord of PNPLA6 and PNPLA7-deficient mice.

Anti-p62 antibody (Guinea pig anti-p62 C-terminal pAb, MBL PM066) 1:1,000 dilution Anti-p62 antibody (Mouse anti-SQSTM1/p62 antibody, abcam, ab56416) 1:1,000 dilution Tetramethylrhodamine α-bungarotoxin (Sigma-Aldrich, T0195) 1.5 μg/ml Anti-neurofilament M antibody (DSHB, AB_2314897) 1:50 dilution Anti-synaptic vesicle 2 antibody (DSHB, AB_2315387) 1:100 dilution Anti-GFAP antibody (Proteintech, 60190-1-IG) 1:1,000 dilution Anti-Mac2 antibody (Rat anti-mouse/human Mac2 antibody, Biolegend, 125410) 1:500 dilution Anti-NeuN antibody (Novus biologicals, NBP1-92693) 1:1,000 dilution Secondary antibodies were F(ab')2-Goat anti-Mouse IgG (H+L) Cross-Adsorbed Secondary Antibody, Alexa Fluor 488 (ThermoFisher Scientific, A-11017) for GFAP staining in FIGS. 5D and 6C, Alexa Fluor (registered trademark) 546 F(ab')2 fragment of goat anti-mouse IgG (H+L) (ThermoFisher Scientific, A-11018) for p62 staining in FIGS. 6A, 6B, and 6D, and Goat anti-Guinea Pig IgG (H+L) Highly Cross-Adsorbed Secondary Antibody, Alexa Fluor 633 (ThermoFisher Scientific, A-21105) for p62 staining in FIG. 6C, each used at 1:1,000 dilution.

VECTASHIELD (registered trademark) Antifade Mounting Medium With DAPI (Vector #H-1200) was used as the mounting medium.

Lipid Analysis

For lipid extraction from the brain, the hemisphere was added with a 20-fold volume of hexane/2-propanol=3:2, homogenized with a bead crusher (Taitec pT-01) and 5 mm stainless steel beads at 4,000 rpm for 60 seconds, further agitated with a vortex mixer for 5 minutes, and then centrifuged at 2,000×g and 4° C. for 10 minutes to collect the supernatant. The precipitate was re-extracted by adding 20-fold volume of hexane/2-propanol=3:2 again, and the resulting supernatant was combined with the previous one. For thin-layer chromatography, lipids derived from the brain (equivalent of 5 mg wet weight) were spotted on one lane of a TLC plate (Silica gel 60, Merck), the composition of the developing solvent was chloroform/methanol/water=65:25:4, and coloration was performed by spraying 5% copper sulfate (in 15% aqueous solution of phosphoric acid) and heating at 180° C.

2. Results

1) Neuron-Specific Pnpla6- and Pnpla7-Deficient Mice (dcKO Mice) Show Growth Failure and Short Lifespan A targeting vector, which consisted of a FRT-LacZ-loxP-Neo-FRT-loxP sequence inserted upstream and a loxP sequence inserted downstream of the target, i.e., exons 7 and 8 of the PNPLA6 gene or exon 26 of the PNPLA7 gene, was introduced into ES cells to select homologous recombinant cells. Chimeric mice and F1 mice were generated and crossed with Flippase overexpressing mice to generate flox/+(f/+) mice. These were further crossed with transgenic mice that expressed the Cre recombinase specifically in nervous system cells under the control of the Nestin promoter to establish (i) Pnpla6$^{f/f}$; Nes-Cre, (ii) Pnpla7$^{f/f}$; Nes-Cre, and (iii) Pnpla6$^{f/f}$; Pnpla7$^{f/f}$; Nes-Cre (hereinafter, double conditional KO=dcKO) and use them for analysis.

Figure 2:
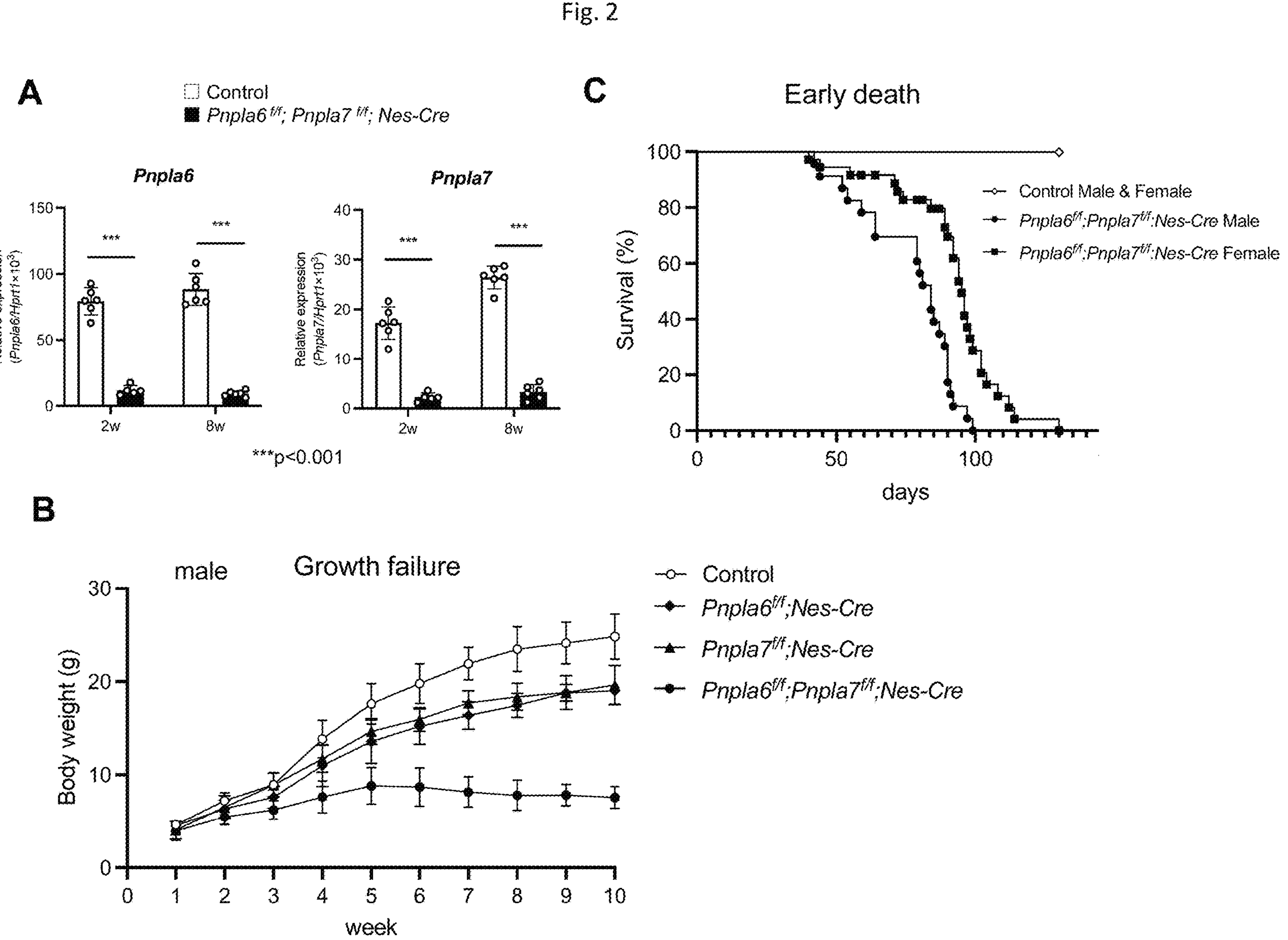
FIG. 2 Figures showing growth failure and survival curves resulting from the central nervous system-specific PNPLA6 and PNPLA7 deficiency.

It was confirmed that the mRNA expression levels of Pnpla6 and Pnpla7 were markedly reduced in cells prepared from dcKO mouse brains (FIG. 2A). The analysis of temporal change in body weight of each group indicated that Pnpl6$^{f/f}$; Nes-Cre and Pnpla7$^{f/f}$; Nes-Cre groups showed slower weight gain than the control group, whereas dcKO mice showed significant growth failure, reaching a peak at 5 weeks of age with no weight gain thereafter (FIG. 2B). Furthermore, only dcKO mice had significantly short lifespan, with many individuals dying early at around 100 days of age (FIG. 2C).

Figure 3:
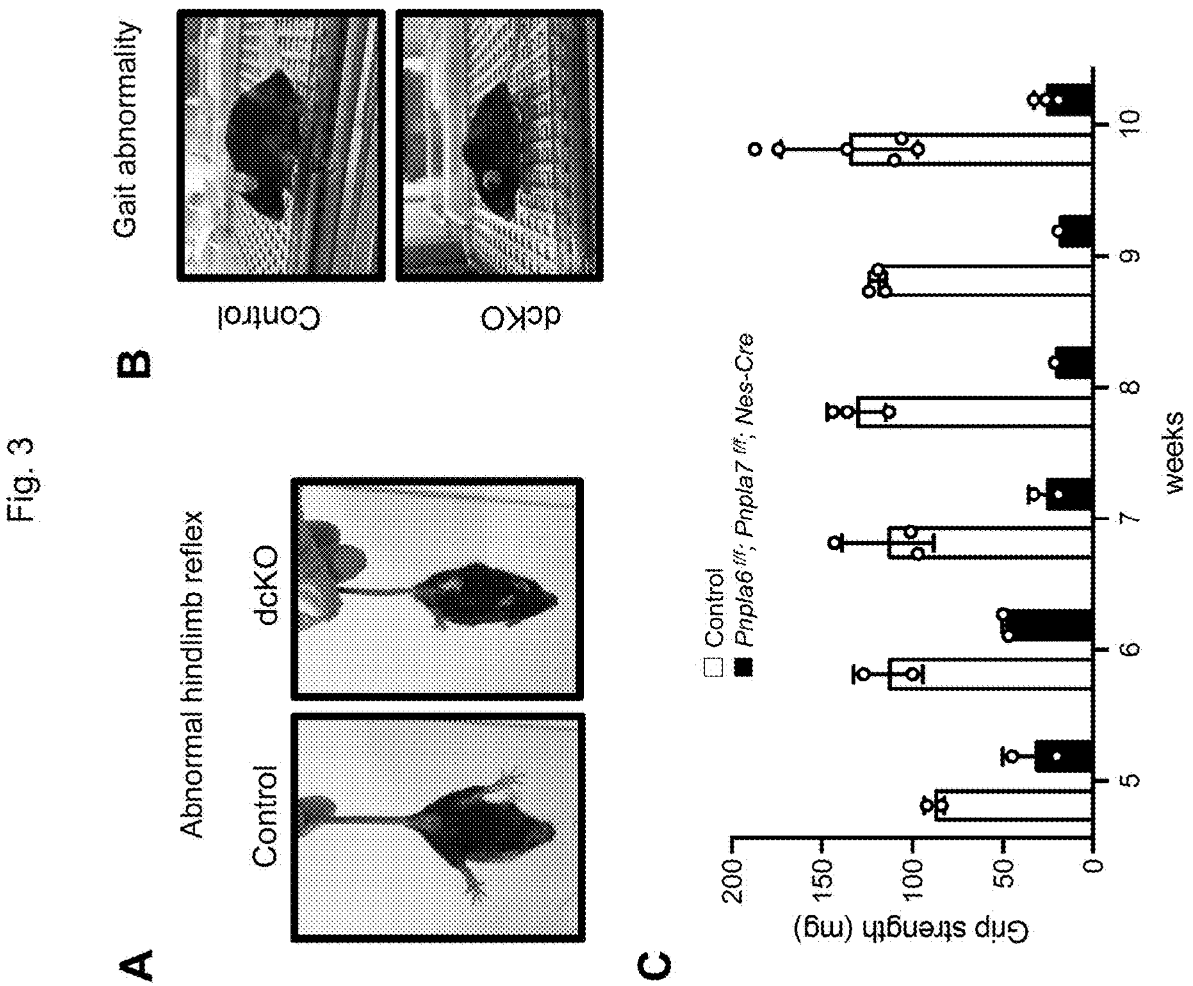
FIG. 3 Figures showing various phenotypes in PNPLA6- and PNPLA7-deficient mice.
Figure 4:
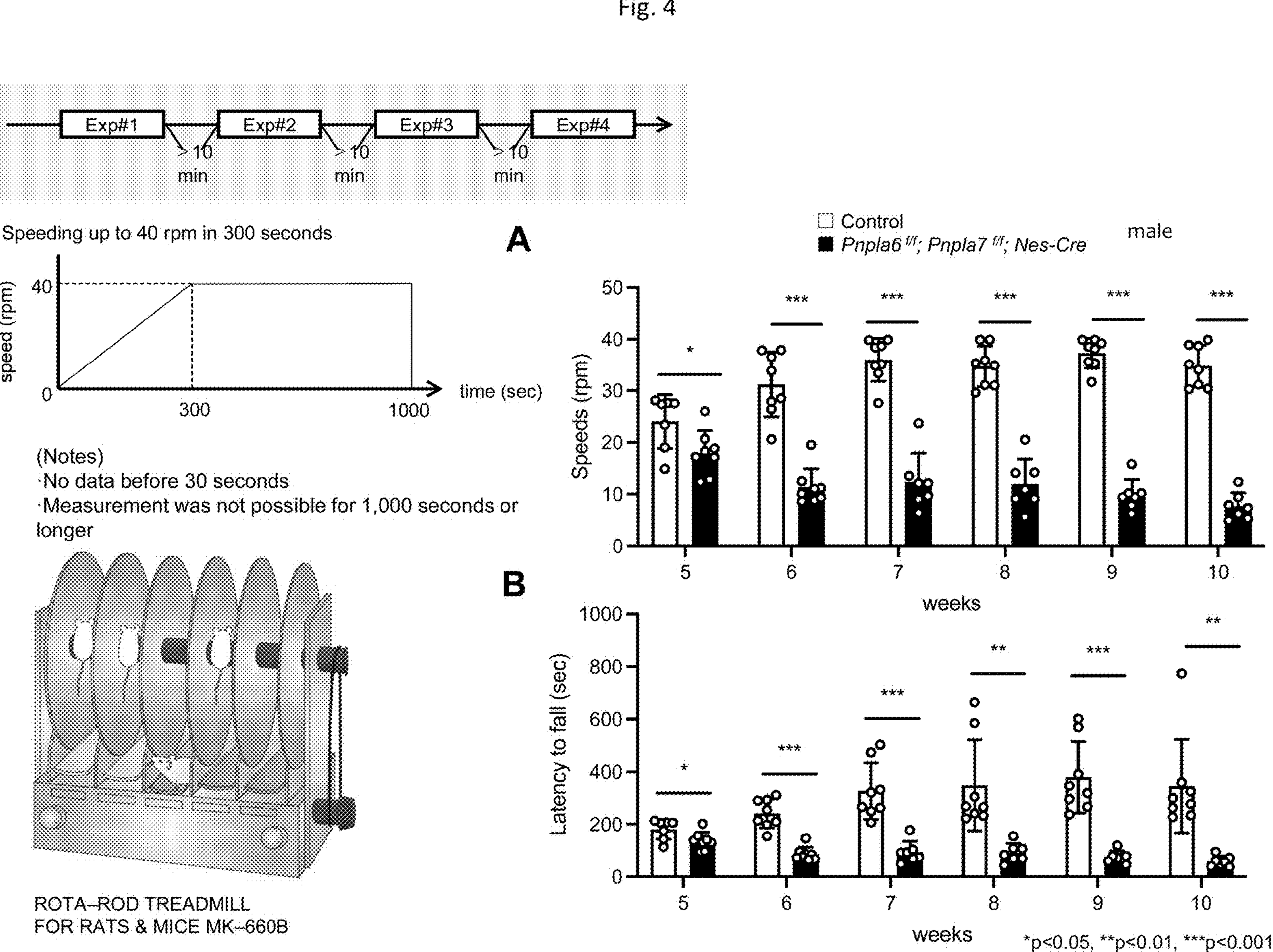
FIG. 4 Figures showing impaired motor coordination skills in PNPLA6- and PNPLA7-deficient mice.

2) Abnormal Hindlimb Reflexes, Gait Abnormality, Decreased Muscle Strength and Motor Coordination Skill dcKO mice showed abnormal hindlimb reflexes called hindlimb clasping (FIG. 3A), exhibited abnormal gait, resting tremor, and hypokinesia with body weight loss (FIG. 3B), and, although there were some differences between individuals, their clinical symptoms gradually worsened from a slow gait with lack of agility, mild unilateral or bilateral incomplete paralysis of the hindlimbs, to severe bilateral paralysis of the hindlimbs with difficulty in moving. In addition, grip strength decreased before 5 weeks of age (FIG. 3C), and when motor coordination was tested by placing the mice on a rotating rod of the Rota-rod and gradually increasing the speed to measure the time until the mice fell off, a gradual decrease in performance in dcKO was observed after 5 weeks of age compared to that in the control group (Pnpla6$^{f/f}$; Pnpla7$^{f/f}$) (FIGS. 4A and 4B). On the other hand, in mice lacking single gene (e.g., Pnpla6$^{f/f}$; Nes-Cre and Pnpla7$^{f/f}$; Nes-Cre), such a decline in motor function was not observed at all, at least before the age of 9 weeks, and according to the previous report, the impairment of motor skill in Pnpla6$^{f/f}$; Nes-Cre mice occurred after the age of 5 months. (Akassoglou K, Malester B, Xu J, Tessarollo L, Rosenbluth J, Chao M V. Brain-specific deletion of neuropathy target esterase/swisscheese results in neurodegeneration. Proc Natl Acad Sci USA 101: 5075-5080, 2004).

3) Amyotrophy, Denervation at Neuromuscular Junction

Since dcKO mice showed decreased motor coordination and grip strength, myofibers were histologically evaluated by observing hematoxylin-eosin-stained tissue sections of the femoral muscles. As a result, the transverse diameters of the myofibers were decreased in dcKO mice by 5 weeks of age, and large-scale and overall group atrophy occurred and an increase in the number of peripheral nuclei was observed by 8 weeks of age (FIG. 5A). The central nuclei seen in atrophic fiber keratinization and myopathy were almost absent, and gene expressions of amyotrophy markers such as Fbxo32 and Trim63 were enhanced (FIG. 5B). At 12 weeks of age, not only was the difference in body size more significant than in the control group, but also the skeletal muscles of the whole body were severely atrophied and the curvature of the spine (arrow) was observed (FIG. 5C).

Furthermore, histological analysis of the neuromuscular junction in the femoral muscle was performed by staining acetylcholine receptors on the skeletal muscle side with red-fluorescently labeled α-bungarotoxin and nerve axons and nerve endings projecting thereto with anti-neurofilament M and anti-synaptic vesicle 2 antibodies (green). As a result, it was found that the projection of the nerve endings at the neuromuscular junction of dcKO mice was significantly reduced and denervation occurred by 10 weeks of age (FIG. 5D). These results indicate that neurogenic amyotrophy occurred in dcKO mice at the same time as a decline in motor function and muscle strength.

4) Neurodegeneration and Changes in Lipid Composition

Figure 7:
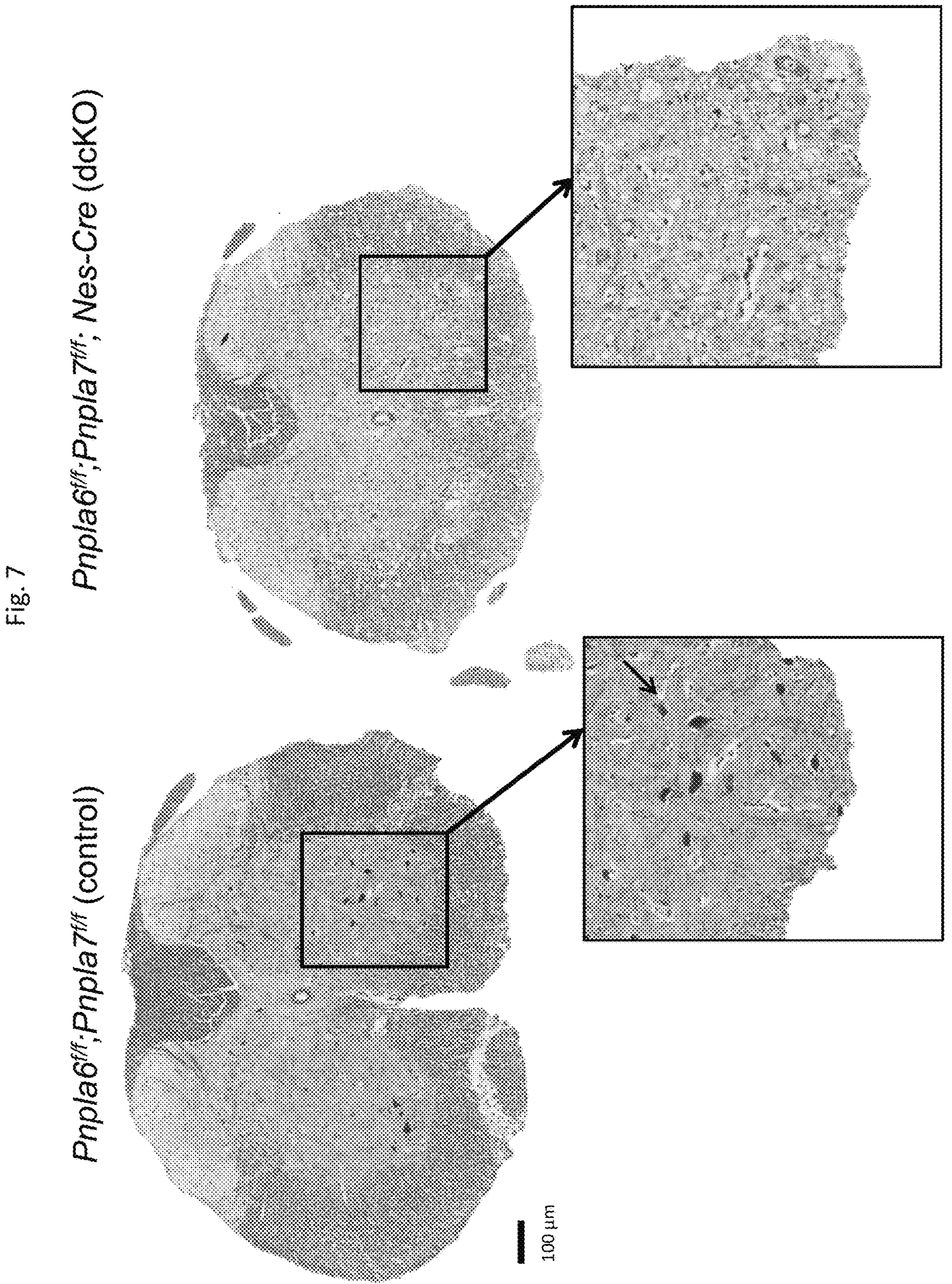
FIG. 7 Figures showing a decrease in motor neurons due to degeneration and loss thereof in the anterior horn of the spinal cord by Kluver-Barrera (KB) staining. In dcKO (right panel), motor neurons characterized by large cell bodies are decreased.

Immunohistological evaluation of abnormalities of the central nervous system revealed that p62-positive aggregates, which accumulate due to autophagy failure and the like, were widely observed mainly in the white matter of the brain and the spinal cord of dcKO mice (arrowheads in FIG. 6A). In the spinal cord, p62-positive aggregates were observed after 3 weeks of age (arrowheads in FIG. 6B), GFAP-positive astrogliosis and an increase in Mac2-positive microglia proceeded with a similar time course, and p62-positive aggregates were often localized in contact with GFAP-positive astroglia (FIG. 6C). Although lower motor neurons project from the anterior hom of the spinal cord, staining of this site with a NeuN-positive neuronal marker revealed a significant decrease in the number of neurons in the anterior horn of the spinal cord after 8 weeks of age (FIG. 6D). A decrease in the motor neurons in the anterior hom of the spinal cord due to degeneration and loss thereof was also observed by Kluver-Barrera (KB) staining (FIG. 7).

Furthermore, thin-layer chromatography for the analysis of lipids extracted from whole brain with hexane/2-propanol=3:2 (the composition of the developing solvent: chloroform/methanol/water=65:25:4) revealed that a series of sphingolipids constituting the myelin sheath, namely galactosylceramide (GalCer), a hydroxylated form thereof (Hydroxy GalCer), sulfatide, sphingomyelin, etc. were decreased to about half in dcKO mice after 5 weeks of age (FIG. 8).

These results were well consistent with the detection of large numbers of p62-positive aggregates in the myelin sheath-rich white matter, suggesting that oligodendrocyte survival and myelination were abnormal in dcKO mice.

On the other hand, the above group of lipids was not decreased in gene-deficient mice lacking either Pnpla6 or Pnpla7 (scKO mice) (FIG. 9).

5) Phenotypes of Mice Lacking Pnpla6 and Pnpla7 in Limited Cell Types

Since Pnpla6$^{f/f}$; Pnpla7$^{f/f}$; Nes-Cre mice express the Cre recombinase under the control of the Nestin promoter, genes Pnpla6 and Pnpla7 are extensively deleted in neurons and glial cells (except microglia). Accordingly, to estimate the contribution of neurons and astroglia in the aforementioned neurodegeneration and amyotrophy, Pnpla6$^{f/f}$; Pnpla7$^{f/f}$; ChAT-Cre mice (ChAT dcKO mice) were generated using the promoter of choline acetyltransferase (ChAT), which is specifically expressed in cholinergic neurons such as motor neurons, and Pnplad$^{f/f}$; Pnpla7$^{f/f}$; GFAP-Cre mice (GFAP dcKO mice) were generated using the promoter of glial fibrillary acidic protein (GFAP), which is expressed in astroglial cells.

When the promoter of ChAT is used, the promoter acts on cholinergic nerves to induce gene expression. Accordingly, introduction of ChAT-Cre into Pnpla6$^{f/f}$; Pnpla7$^{f/f}$ mice results in cholinergic neuron-specific expression of the Cre recombinase under the control of the ChAT promoter and recombination of the sequence flanked by loxP sequences in these cells, thereby obtaining ChAT dcKO mice that lack PNPLA6 and PNPLA7 in a cholinergic neuron-specific manner.

When the promoter of GFAP is used, the promoter acts on astrocytes to induce gene expression. Accordingly, introduction of GFAP-Cre into Pnpla6$^{f/f}$; Pnpla7$^{f/f}$ mice results in astrocyte-specific expression of the Cre recombinase under the control of the GFAP promoter and recombination of the sequence flanked by loxP sequences in these cells, thereby obtaining GFAP dcKO mice that lack PNPLA6 and PNPLA7 in an astrocyte-specific manner.

ChAT dcKO mice showed curvature of the spine at 8 weeks of age, followed by abnormal lower limb reflexes, and they showed slower weight gain than the control mice and developed gait abnormality and amyotrophy from around 3 to 4 months of age (FIG. 10). Unlike Pnpla6$^{f/f}$; Pnpla7$^{f/f}$; Nes-Cre mice, p62-positive aggregates were absent in ChAT dcKO mice and they were fertile in both sexes.

On the other hand, about a quarter of GFAP dcKO mice showed neurodegeneration and amyotrophy, while no obvious abnormalities could be detected by appearance in the remaining individuals. The former showed resting tremor from around 8 weeks of age, with loss of motor neurons in the spinal cord, and p62-positive aggregates in the white and gray matter (FIG. 11). In these mice, positive findings of abnormally phosphorylated TDP-43 (pSer409/410), which has been reported to accumulate in degenerating neurons and glial cells in neurological diseases such as amyotrophy lateral sclerosis (ALS) and frontotemporal lobar degeneration (FTLD), were also observed in the gray matter (FIG. 11).

The subsequent course of GFAP dcKO mice was similar to that of dcKO (Pnpla6$^{f/f}$; Pnpla7$^{f/f}$; Nes-Cre) mice, where they showed gait abnormalities with marked weight loss and progressive amyotrophy (FIG. 12). Even in apparently normal individuals, p62-positive aggregates were significantly increased only in the white matter of the spinal cord, but no abnormally phosphorylated TDP-43 in the gray matter or loss of motor neurons was observed (FIG. 11). In addition, GFAP dcKO mice did not show curvature of the spine that occurred in dcKO and ChAT dcKO mice.

These results indicate that the lack of both lysophospholipases PNPLA6 and PNPLA7 throughout the central nervous system causes extensive neurodegeneration in the brain and spinal cord accompanied by abnormal activation and proliferation of the astrocytes, activation of microglia, accumulation of p62-positive aggregates, an increase in phosphorylated TDP-43 aggregates, a decrease in the group of sphingolipids in the myelin sheath, etc., as well as loss of motor neurons in the anterior horn of the spinal cord, severe neurogenic amyotrophy, and body weight loss.

On the other hand, when both enzymes were deleted in a cholinergic neuron-specific manner, the onset of amyotrophy and gait abnormalities was greatly delayed, whereas curvature of the spine occurred early. When both enzymes were deleted in an astroglia-specific manner, about a quarter of the individuals showed progression of pathological conditions including neurodegeneration, a decline in muscle strength, amyotrophy, and gait abnormalities. Thus, PNPLA6 and PNPLA7 were found to function in both neurons and astrocytes and the contribution of enzyme deficiency in astroglia was found to be significant for the early neurodegeneration, amyotrophy, and formation of p62-positive aggregates.

3. Discussion

The results of the present invention have shown that when PNPLA6 and PNPLA7, which possess lysophospholipase activity, are deleted in a nervous system-specific manner, extensive neurodegeneration and severe amyotrophy are caused. Since abnormalities in enzymes that metabolize phospholipids, cholesterol, sphingolipids, etc. are closely related to degeneration of motor neurons, etc. (Rickman O J, Baple E L, Crosby A H. Lipid metabolic pathways converge in motor neuron degenerative diseases. Brain 43: 1073-1087, 2020), many related studies have been conducted. However, the essential molecular mechanisms that lead to the degeneration are not fully understood, and there is currently no effective treatment.

For example, human diseases that cause neurogenic amyotrophy accompanied by degeneration of motor neurons include amyotrophic sclerosis (ALS), frontotemporal lobar degeneration (FTLD), and spinal muscular atrophy (SMA), all of which are progressive, intractable neurological diseases. In severe types, patients eventually die of respiratory muscle failure, and no effective treatment has been established. Among these motor neuron diseases, ALS is the most common, and it is estimated that there are about 10,000 patients in Japan and nearly 300,000 patients worldwide. Because the disorder affects all voluntary muscles in the body, the onset of ALS places a heavy burden not only on the patient but also on family members, and since half of the patients with this intractable disease die of respiratory paralysis within a few years after the onset of the disease, establishment of a novel treatment method is urgently needed.

As ALS model animals for research purposes, rodents introduced with superoxide dismutase 1 (SOD1), which is a frequently mutated gene in familial ALS in Japan, hexanucleotide repeat expansion in C9ORF72, which is the most common cause of familial ALS in the U.S. and Europe, mutation in RNA-binding protein FUS (fused in sarcoma), or mutation in TDP-43 (TAR DNA-binding protein-43) are frequently used, and the molecular mechanisms of degeneration of motor neurons caused by these mutations have been intensively analyzed. (Rudnick N D, Griffey C J, Guarieri P, Valeria Gerbino V, Wang X, Piersaint J A, Tapia J C, Rich M M, Maniatis T. Distinct roles for motor neuron autophagy early and late in the SOD1G93A mouse model of ALS. Proc Natl Acad Sci USA, 114: E58294-8303, 2017). At present, however, the pathophysiology of ALS has not yet been elucidated and no fundamental treatment has been established. In fact, these model animals obtained by directly introducing human-derived mutations into rodents (for example, transgenic mice overexpressing a high copy number (20 to 30 copies) of the most commonly used human mutant SOD1 gene with the G93A point mutation) have less severe levels of symptoms including amyotrophy and have limited applicability for elucidating the pathophysiology and studying therapeutic drugs.

In contrast, the present inventors have established dcKO mice lacking two lysophospholipases, PNPLA6 and PNPLA7, in a nervous system-specific manner, which are characterized not only by a rapid progression of neurodegeneration and a short lifespan but also by severe neurogenic amyotrophy that leads to difficulty in walking (FIG. 13).

Furthermore, ChAT dcKO mice lacking both genes Pnpla6 and Pnpla7 in a cholinergic neuron-specific manner are characterized by the late onset and the ability to reproduce as deficient mice. Meanwhile, GFAP dcKO mice are characterized by the accumulation of abnormally phosphorylated TDP-43 and p62-positive aggregates in the spinal cord, and only some individuals develop neurodegeneration and amyotrophy (FIG. 15), and thus can be used as a model of sporadic neurodegeneration disease.

Therefore, the group of gene-deficient mice targeting lysophospholipases generated in this study are considered to be highly useful as novel disease model animals for elucidating the molecular mechanism of neurogenic amyotrophy, and screening of therapeutic drug candidates for the disease and analyzing the mechanism of action of the drugs.

[Sequence Listing Free Text]

SEQ ID NOS:1-18: Synthetic DNA primers

The invention claimed is:

1. A neurodegenerative disease model animal with amyotrophy, comprising a nonhuman animal deficient in both the PNPLA6 and PNPLA7 genes wherein PNPLA6 and PNPLA7 genes are deleted in a neuron- or glial-cell-specific manner.

2. The animal according to claim 1, wherein the amyotrophy is neurogenic amyotrophy.

3. The animal according to claim 2, wherein a symptom of the neurodegenerative disease is accompanied by at least one selected from the group consisting of shortened lifespan, body weight loss, impaired motor skill, gait abnormality, resting tremor, spasticity, abnormal hindlimb reflex, amyotrophy, curvature of the spine, loss of motor neurons, degeneration of neuromuscular junction, activation of astrocytes, activation of microglia, accumulation of p62-positive aggregates, accumulation of phosphorylated TDP-43 aggregates, and decreases in sphingolipids in the myelin sheath.

4. The animal according to claim 1, wherein the neuron is a cholinergic neuron.

5. The animal according to claim 4, wherein a symptom of the neurodegenerative disease is accompanied by at least one selected from the group consisting of a shortened lifespan, body weight loss, impaired motor skill, gait abnormality, abnormal hindlimb reflex, amyotrophy, curvature of the spine, abnormal hindlimb reflex, activation of astrocytes, and activation of microglia.

6. The animal according to claim 1, wherein the glial cell is an astroglial cell.

7. The animal according to claim 6, wherein a symptom of the neurodegenerative disease is accompanied by at least one selected from the group consisting of a shortened lifespan, body weight loss, impaired motor skill, gait abnormality, resting tremor, spasticity, abnormal hindlimb reflex, amyotrophy, curvature of the spine, loss of motor neurons, degeneration of neuromuscular junction, activation of astrocytes, activation of microglia, accumulation of p62-positive aggregates, and accumulation of phosphorylated TDP-43 aggregates.

8. The animal according to claim 1, wherein the nonhuman animal is a mouse, rat, rabbit, dog, cat, pig, marmoset, or monkey.

9. A model cell or organoid for a neurodegenerative disease with amyotrophy, comprising an animal cell deficient in both the PNPLA6 and PNPLA7 genes.

10. The model cell or organoid according to claim 9, in which the PNPLA6 and PNPLA7 genes are deleted in a neuron-and/or glial cell-specific manner.

11. The model cell or organoid according to claim 10, wherein the neuron is a cholinergic neuron.

12. The model cell or organoid according to claim 10, wherein the glial cell is an astroglial cell.

13. A method for screening a drug for a neurodegenerative disease, the method comprising the steps of: contacting a test substance with the animal according to claim 1 or a biological sample collected from said animal; and if an effect of amelioration of neurodegeneration is obtained in said nonhuman animal or biological sample after its contact with the test substance, then selecting the test substance as a drug for a neurodegeneration disease.

14. A method for screening a drug for a disease with amyotrophy, the method comprising the steps of: contacting a test substance with the animal according to claim 1 or a biological sample collected from said animal; and if an effect of amelioration of amyotrophy is obtained in said nonhuman animal or biological sample, after its contact with the test substance, then selecting the test substance as a drug for a disease with amyotrophy.

15. The method according to claim 14, wherein amyotrophy is neurogenic amyotrophy.

16. The method according to claim 15, wherein the disease with neurogenic amyotrophy is at least one selected from the group consisting of amyotrophic lateral sclerosis, primary lateral sclerosis, frontotemporal lobar degeneration, spinal muscular atrophy, spinal progressive muscular atrophy, spinobulbar muscular atrophy, spastic paraplegia, and multifocal motor neuropathy.

17. A method for screening a drug for a neurodegenerative disease, the method comprising the steps of: contacting a test substance with the model cell or organoid according to claim 9; and if an effect of amelioration of neurodegeneration is obtained in model cell or organoid after its contact with the test substance, then selecting the test substance as a drug for a neurodegeneration disease.

18. A method for screening a drug for a disease with amyotrophy, the method comprising the steps of: contacting a test substance with the model cell or organoid according to claim 9; and if an effect of amelioration of amyotrophy is obtained in said model cell or organoid after its contact with the test substance, then selecting the test substance as a drug for a disease with amyotrophy.

* * * * *

SEQUENCE LISTING

```
Sequence total quantity: 18
SEQ ID NO: 1              moltype = DNA  length = 20
FEATURE                   Location/Qualifiers
misc_feature              1..20
                          note = Synthetic DNA
source                    1..20
                          mol_type = other DNA
                          organism = synthetic construct
SEQUENCE: 1
acttgcctgt tatgtgtagg                                                  20

SEQ ID NO: 2              moltype = DNA  length = 20
FEATURE                   Location/Qualifiers
misc_feature              1..20
                          note = Synthetic DNA
source                    1..20
                          mol_type = other DNA
                          organism = synthetic construct
SEQUENCE: 2
tgatgacatc aaggatgctc                                                  20

SEQ ID NO: 3              moltype = DNA  length = 20
FEATURE                   Location/Qualifiers
misc_feature              1..20
                          note = Synthetic DNA
source                    1..20
                          mol_type = other DNA
                          organism = synthetic construct
SEQUENCE: 3
ccctggttca attcccagta                                                  20

SEQ ID NO: 4              moltype = DNA  length = 20
FEATURE                   Location/Qualifiers
misc_feature              1..20
                          note = Synthetic DNA
source                    1..20
                          mol_type = other DNA
                          organism = synthetic construct
SEQUENCE: 4
ggagtttgca tgaccacaga                                                  20
```

```
SEQ ID NO: 5            moltype = DNA  length = 21
FEATURE                 Location/Qualifiers
misc_feature            1..21
                        note = Synthetic DNA
source                  1..21
                        mol_type = other DNA
                        organism = synthetic construct
SEQUENCE: 5
ccttcctgaa gcagtagagc a                                            21

SEQ ID NO: 6            moltype = DNA  length = 20
FEATURE                 Location/Qualifiers
misc_feature            1..20
                        note = Synthetic DNA
source                  1..20
                        mol_type = other DNA
                        organism = synthetic construct
SEQUENCE: 6
gccttattgt ggaaggactg                                              20

SEQ ID NO: 7            moltype = DNA  length = 27
FEATURE                 Location/Qualifiers
misc_feature            1..27
                        note = Synthetic DNA
source                  1..27
                        mol_type = other DNA
                        organism = synthetic construct
SEQUENCE: 7
tgatagatcc attcctatga ctgtaga                                      27

SEQ ID NO: 8            moltype = DNA  length = 27
FEATURE                 Location/Qualifiers
misc_feature            1..27
                        note = Synthetic DNA
source                  1..27
                        mol_type = other DNA
                        organism = synthetic construct
SEQUENCE: 8
aagacattct ttccagttaa agttgag                                      27

SEQ ID NO: 9            moltype = DNA  length = 20
FEATURE                 Location/Qualifiers
misc_feature            1..20
                        note = Synthetic DNA
source                  1..20
                        mol_type = other DNA
                        organism = synthetic construct
SEQUENCE: 9
tgccagcatc tatgtggttc                                              20

SEQ ID NO: 10           moltype = DNA  length = 20
FEATURE                 Location/Qualifiers
misc_feature            1..20
                        note = Synthetic DNA
source                  1..20
                        mol_type = other DNA
                        organism = synthetic construct
SEQUENCE: 10
cacacactcc ttcccatcag                                              20

SEQ ID NO: 11           moltype = DNA  length = 18
FEATURE                 Location/Qualifiers
misc_feature            1..18
                        note = Synthetic DNA
source                  1..18
                        mol_type = other DNA
                        organism = synthetic construct
SEQUENCE: 11
ggagggggtg gagctaga                                                18

SEQ ID NO: 12           moltype = DNA  length = 19
FEATURE                 Location/Qualifiers
misc_feature            1..19
                        note = Synthetic DNA
source                  1..19
                        mol_type = other DNA
                        organism = synthetic construct
SEQUENCE: 12
```

-continued

```
cgccacactc tgctagtgc                                          19

SEQ ID NO: 13           moltype = DNA  length = 20
FEATURE                 Location/Qualifiers
misc_feature            1..20
                        note = Synthetic DNA
source                  1..20
                        mol_type = other DNA
                        organism = synthetic construct
SEQUENCE: 13
ggggagctgt gatgtgaagt                                         20

SEQ ID NO: 14           moltype = DNA  length = 22
FEATURE                 Location/Qualifiers
misc_feature            1..22
                        note = Synthetic DNA
source                  1..22
                        mol_type = other DNA
                        organism = synthetic construct
SEQUENCE: 14
ccaggaaata attctggctc at                                      22

SEQ ID NO: 15           moltype = DNA  length = 20
FEATURE                 Location/Qualifiers
misc_feature            1..20
                        note = Synthetic DNA
source                  1..20
                        mol_type = other DNA
                        organism = synthetic construct
SEQUENCE: 15
agtgaggacc ggctactgtg                                         20

SEQ ID NO: 16           moltype = DNA  length = 20
FEATURE                 Location/Qualifiers
misc_feature            1..20
                        note = Synthetic DNA
source                  1..20
                        mol_type = other DNA
                        organism = synthetic construct
SEQUENCE: 16
gatcaaacgc ttgcgaatct                                         20

SEQ ID NO: 17           moltype = DNA  length = 22
FEATURE                 Location/Qualifiers
misc_feature            1..22
                        note = Synthetic DNA
source                  1..22
                        mol_type = other DNA
                        organism = synthetic construct
SEQUENCE: 17
tgacatctac aagcaggagt gc                                      22

SEQ ID NO: 18           moltype = DNA  length = 19
FEATURE                 Location/Qualifiers
misc_feature            1..19
                        note = Synthetic DNA
source                  1..19
                        mol_type = other DNA
                        organism = synthetic construct
SEQUENCE: 18
tcgtcttcgt gttccttgc                                          19
```